(12) United States Patent
Asif et al.

(10) Patent No.: US 9,804,072 B2
(45) Date of Patent: Oct. 31, 2017

(54) HIGH TEMPERATURE HEATING SYSTEM

(71) Applicant: Hysitron, Inc., Eden Prairie, MN (US)

(72) Inventors: Syed Amanulla Syed Asif, Bloomington, MN (US); Edward Cyrankowski, Woodbury, MN (US); Lucas Paul Keranen, Hutchinson, MN (US); Ryan Major, Crystal, MN (US); Yunje Oh, Medina, MN (US); Oden Lee Warren, New Brighton, MN (US); Maciej W. Misiak, Eden Prairie, MN (US)

(73) Assignee: Hysitron, Inc., Eden Prairie, MN (US)

( * ) Notice: Subject to any disclaimer, the term of this patent is extended or adjusted under 35 U.S.C. 154(b) by 163 days.

(21) Appl. No.: 14/361,133

(22) PCT Filed: Nov. 28, 2012

(86) PCT No.: PCT/US2012/066842
§ 371 (c)(1),
(2) Date: May 28, 2014

(87) PCT Pub. No.: WO2013/082145
PCT Pub. Date: Jun. 6, 2013

(65) Prior Publication Data
US 2015/0033835 A1    Feb. 5, 2015

Related U.S. Application Data

(60) Provisional application No. 61/564,188, filed on Nov. 28, 2011.

(51) Int. Cl.
*G01N 3/42* (2006.01)
*G01N 3/54* (2006.01)
(Continued)

(52) U.S. Cl.
CPC ............. *G01N 3/54* (2013.01); *G01N 3/08* (2013.01); *G01N 3/18* (2013.01); *H05B 1/023* (2013.01);
(Continued)

(58) Field of Classification Search
CPC .. G01N 3/08; G01N 3/18; G01N 3/54; G01N 2203/0078; G01N 2203/0226;
(Continued)

(56) References Cited

U.S. PATENT DOCUMENTS 3,028,754 A    4/1962  Huyser
3,896,314 A    7/1975  Nukui et al.
(Continued)

FOREIGN PATENT DOCUMENTS

EP    0855452 A1    7/1998
EP    2011066018 A1    6/2011
(Continued)

OTHER PUBLICATIONS

"U.S. Appl. No. 13/510,825, Notice of Allowance mailed Jan. 29, 2016", 7 pgs.
(Continued)

*Primary Examiner* — Harshad R Patel
*Assistant Examiner* — Brandi Hopkins
(74) *Attorney, Agent, or Firm* — Schwegman Lundberg & Woessner, P.A.

(57) ABSTRACT

A heating system for use in mechanical testing at scales of microns or less includes a stage heater. The stage heater having a stage plane, and a stage heating element distributed across the stage plane. Two or more support mounts are on opposed sides of the stage plane. A first bridge extends from the stage plane to a first mount of the two or more support mounts, and a second bridge extends from the stage plane to a second mount of the two or more support mounts. The first
(Continued)

and second bridges provide a plurality of supports between the stage plane and two or more support mounts to accordingly support the stage plane. In another example, the heating system includes a probe heater configured to heat a probe as part of mechanical testing.

21 Claims, 7 Drawing Sheets

(51) Int. Cl.
  *G01N 3/18* (2006.01)
  *G01N 3/08* (2006.01)
  *H05B 1/02* (2006.01)
  *H05B 3/32* (2006.01)

(52) U.S. Cl.
  CPC ....... *H05B 3/32* (2013.01); *G01N 2203/0078* (2013.01); *G01N 2203/0226* (2013.01); *G01N 2203/0282* (2013.01); *G01N 2203/0286* (2013.01); *G01N 2203/0482* (2013.01)

(58) Field of Classification Search
  CPC ... G01N 2203/0282; G01N 2203/0286; G01N 2203/0482; G01N 3/40; G01N 3/42; G01N 2203/0647; G01N 2203/0222; G01N 3/04; G01N 2203/0019; G01N 33/388; H05B 1/023; H05B 3/32; H05B 3/03; H05B 3/0014; H05B 6/10; G01Q 30/02; G01Q 60/366; G01Q 30/10; G01Q 3/42; H01J 37/20; B81C 99/005; G01L 1/005
  USPC .......... 73/82, 859–860, 856, 760, 766, 790; 219/201, 536, 50; 374/50–51
  See application file for complete search history.

(56) References Cited

U.S. PATENT DOCUMENTS

| | | | |
|---|---|---|---|
| 4,346,754 A | 8/1982 | Imig et al. |
| 4,474,015 A | 10/1984 | Christmas et al. |
| 4,491,788 A | 1/1985 | Zandonatti |
| 4,703,181 A | 10/1987 | Swann et al. |
| 4,735,092 A | 4/1988 | Kenny |
| 4,820,051 A | 4/1989 | Yanagisawa et al. |
| 4,917,462 A | 4/1990 | Lewis et al. |
| 4,992,660 A | 2/1991 | Kobayashi |
| 4,996,433 A | 2/1991 | Jones et al. |
| 5,015,825 A | 5/1991 | Brindley |
| 5,202,542 A | 4/1993 | Ferguson |
| 5,331,134 A | 7/1994 | Kimura |
| 5,367,171 A | 11/1994 | Aoyama et al. |
| 5,507,189 A | 4/1996 | Kim et al. |
| 5,512,727 A | 4/1996 | Myers et al. |
| 5,553,486 A | 9/1996 | Bonin |
| 5,654,546 A | 8/1997 | Lindsay |
| 5,661,235 A | 8/1997 | Bonin |
| 5,731,587 A | 3/1998 | Dibattista et al. |
| 5,821,545 A | 10/1998 | Lindsay et al. |
| 5,869,751 A | 2/1999 | Bonin |
| 6,026,677 A | 2/2000 | Bonin |
| 6,339,958 B1 | 1/2002 | Tsui et al. |
| 6,495,838 B1 | 12/2002 | Yaguchi et al. |
| 6,520,004 B1 | 2/2003 | Lin |
| 6,840,305 B2 | 1/2005 | Zheng et al. |
| 7,274,450 B1 | 9/2007 | Green et al. |
| 7,451,636 B2 | 11/2008 | Bradshaw et al. |
| 7,674,037 B2 | 3/2010 | Liu et al. |
| 7,685,868 B2 | 3/2010 | Woirgard et al. |
| 7,685,869 B2 | 3/2010 | Bonilla et al. |
| 7,798,011 B2 | 9/2010 | Warren et al. |
| 7,878,071 B2 | 2/2011 | Greer |
| 8,042,405 B2 | 10/2011 | Shuaib et al. |
| 8,065,929 B2 | 11/2011 | Yakimoski et al. |
| 8,161,803 B2 | 4/2012 | Oh et al. |
| 8,434,370 B2 | 5/2013 | Oh et al. |
| 8,474,324 B2 | 7/2013 | Rihan et al. |
| 8,479,589 B2 | 7/2013 | Shuaib et al. |
| 8,569,714 B2 | 10/2013 | Han et al. |
| 8,631,687 B2 | 1/2014 | Patten et al. |
| 8,844,368 B2 | 9/2014 | Peecock et al. |
| 9,189,592 B2 | 11/2015 | Nam et al. |
| 9,316,569 B2 | 4/2016 | Oh et al. |
| 9,476,816 B2 | 10/2016 | Schmitz et al. |
| 9,759,641 B2 | 9/2017 | Oh et al. |
| 2002/0110177 A1 | 8/2002 | Nakayama et al. |
| 2003/0140684 A1 | 7/2003 | Broz et al. |
| 2006/0025002 A1 | 2/2006 | Zhang et al. |
| 2006/0180577 A1 | 8/2006 | Lindeman |
| 2007/0180924 A1 | 8/2007 | Warren et al. |
| 2007/0278420 A1 | 12/2007 | Molhave |
| 2008/0092938 A1 | 4/2008 | Majumdar et al. |
| 2008/0169428 A1 | 7/2008 | Schoenlein |
| 2008/0266653 A1 | 10/2008 | Korpinen et al. |
| 2008/0276727 A1 | 11/2008 | Enoksson et al. |
| 2008/0290290 A1 | 11/2008 | Nagakubo et al. |
| 2009/0044609 A1 | 2/2009 | Sawa et al. |
| 2009/0111701 A1 | 4/2009 | Ahn et al. |
| 2009/0120172 A1 | 5/2009 | Bradshaw et al. |
| 2009/0194689 A1 | 8/2009 | Abramson et al. |
| 2009/0206258 A1 | 8/2009 | Kasai et al. |
| 2009/0289050 A1 | 11/2009 | Ondricek |
| 2010/0095780 A1 | 4/2010 | Oh et al. |
| 2010/0107745 A1 | 5/2010 | Bonin |
| 2010/0132441 A1 | 6/2010 | Oh et al. |
| 2010/0180356 A1 | 7/2010 | Bonilla et al. |
| 2010/0186520 A1 | 7/2010 | Wheeler, IV et al. |
| 2010/0212411 A1 | 8/2010 | Passilly et al. |
| 2010/0294147 A1 | 11/2010 | Loiret-bernal et al. |
| 2011/0107472 A1 | 5/2011 | Han et al. |
| 2011/0152724 A1 | 6/2011 | Hansma et al. |
| 2011/0252874 A1 | 10/2011 | Patten et al. |
| 2011/0277555 A1 | 11/2011 | Peecock et al. |
| 2011/0277556 A1 | 11/2011 | Peecock et al. |
| 2012/0292528 A1 | 11/2012 | Oh et al. |
| 2013/0098145 A1 | 4/2013 | Oh et al. |
| 2014/0293293 A1 | 10/2014 | Vodnick et al. |
| 2014/0326707 A1 | 11/2014 | Schmitz et al. |
| 2014/0331782 A1 | 11/2014 | Keranen et al. |
| 2015/0179397 A1 | 6/2015 | Damiano, Jr. et al. |
| 2015/0185117 A1 | 7/2015 | Schmitz |
| 2016/0123859 A1 | 5/2016 | Oh et al. |

FOREIGN PATENT DOCUMENTS

| | | |
|---|---|---|
| EP | 2861934 A | 4/2015 |
| EP | 2780689 B1 | 1/2017 |
| EP | 286193431 | 5/2017 |
| GB | 2116459 A | 9/1993 |
| JP | 4996867 A | 12/1972 |
| JP | 4996867 U | 8/1974 |
| JP | 55088256 A | 7/1980 |
| JP | 5691598 A | 7/1981 |
| JP | 57201953 A | 12/1982 |
| JP | 6327731 A | 3/1983 |
| JP | 58173159 A | 10/1983 |
| JP | 58173159 U | 11/1983 |
| JP | 5915635 A | 1/1984 |
| JP | 60127540 A | 7/1985 |
| JP | 181553 U | 5/1989 |
| JP | 01081553 U | 5/1989 |
| JP | 01119153 A | 5/1989 |
| JP | 0366122 A | 3/1991 |
| JP | 04131741 A | 5/1992 |
| JP | 0566186 A | 3/1993 |
| JP | 0572457 A | 3/1993 |
| JP | 06315299 A | 11/1994 |
| JP | 2000241325 A | 9/2000 |
| JP | 2000241332 A | 9/2000 |
| JP | 2000314692 A | 11/2000 |
| JP | 2002116130 A | 4/2002 |
| JP | 2002318318 A | 10/2002 |

(56) References Cited

FOREIGN PATENT DOCUMENTS

| JP | 2008512841 A | 4/2008 |
|---|---|---|
| JP | 2008134191 A | 6/2008 |
| JP | 2008197000 A | 8/2008 |
| JP | 2009526230 A | 7/2009 |
| JP | 2009193833 A | 8/2009 |
| JP | 2013512545 A | 4/2013 |
| JP | 2015501935 A | 1/2015 |
| JP | 6162770 | 6/2017 |
| WO | WO-2008061224 A1 | 5/2008 |
| WO | WO-2011066018 A1 | 6/2011 |
| WO | WO-2011104529 A1 | 9/2011 |
| WO | WO-2013074623 A1 | 5/2013 |
| WO | WO-2013082145 A1 | 6/2013 |
| WO | WO-2013082148 A1 | 6/2013 |
| WO | WO-2013187972 A1 | 12/2013 |

OTHER PUBLICATIONS

"U.S. Appl. No. 14/948,549, Preliminary Amendment filed Jan. 14, 2016", 9 pgs.
"European Application Serial No. 12853899.8, Response filed Jan. 26, 2016 to Extended European Search Report mailed Jun. 29, 2015", 12 pgs.
"International Application Serial No. PCT/US2012/066842, International Search Report mailed Feb. 7, 2013", 2 pgs.
"International Application Serial No. PCT/US2012/066842, Written Opinion mailed Feb. 7, 2013", 8 pgs.
"International Application Serial No. PCT/US2012/066846, International Search Report mailed Feb. 6, 2013", 2 pgs.
"International Application Serial No. PCT/US2012/066846, Written Opinion mailed Feb. 6, 2013", 8 pgs.
"U.S. Appl. No. 13/510,825, Examiner Interview Summary mailed Nov. 18, 2014", 3 pgs.
"U.S. Appl. No. 13/510,825, Final Office Action mailed Dec. 26, 2014", 17 pgs.
"U.S. Appl. No. 13/510,825, Notice of Allowance mailed Aug. 28, 2015", 8 pgs.
"U.S. Appl. No. 13/510,825, Response filed Mar. 25, 2015 to Final Office Action mailed Dec. 26, 2014", 22 pgs.
"U.S. Appl. No. 13/510,825, Response filed Nov. 19, 2014 to Non Final Office Action mailed Jun. 3, 2014", 20 pgs.
"U.S. Appl. No. 14/358,065, Non Final Office Action mailed Jul. 31, 2015", 12 pgs.
"U.S. Appl. No. 14/358,065, Response filed Jun. 17, 2015 to Restriction Requirement mailed Apr. 20, 2015", 14 pgs.
"U.S. Appl. No. 14/358,065, Restriction Requirement mailed Apr. 20, 2015", 7 pgs.
"U.S. Appl. No. 14/407,783, Preliminary Amendment filed Dec. 12, 2014", 13 pgs.
"European Application Serial No. 12849761.7, Extended European Search Report mailed Aug. 7, 2015", 7 pgs.
"European Application Serial No. 12853899.8, Extended European Search Report mailed Jun. 29, 2015", 9 pgs.
"European Application Serial No. 12853965.7, Non Final Office Action mailed Sep. 9, 2015", 5 pgs.
"International Application Serial No. PCT/US2013/031650, International Preliminary Report on Patentability mailed Dec. 24, 2014", 6 pgs.
"Japanese Application Serial No. 2012-541077, Office Action mailed Jan. 6, 2015", W/ English Translation, 4 pgs.
"Japanese Application Serial No. 2012-541077, Response filed Apr. 2, 2015 to Office Action mailed Jan. 6, 2015", W/ English Translations, 13 pgs.
"Japanese Application Serial No. 2012-541077, Response filed Jun. 17, 2014 to Office Action mailed Mar. 18, 2014", with English translation of claims, 10 pgs.
"Japanese Application Serial No. 2014-541415, Office Action mailed Dec. 2, 2014", W/ English Translation, 6 pgs.
"Japanese Application Serial No. 2014-541415, Response Office Action mailed Dec. 2, 2014", W/ English Claims, 6 pgs.
"Japanese Application Serial No. 2014-543623. Voluntary Amendment filed Jul. 29, 2014", W/ English Claims, 18 Pgs.
"Japanese Application Serial No. 2014-543624, Voluntary Amendment filed Jul. 29, 2014", W/ English Claims, 14 pgs.
"Japanese Application Serial No. 2015-517243, Amendment filed Jan. 30, 2015", W/ English Translation.
"Japanese Application Serial No. 2015-517243, Office Action mailed Jun. 16, 2015", W/ English Translation, 9 pgs.
"Japanese Application Serial No. 2015-517243, Response filed Sep. 4, 2015 to Office Action mailed Jun. 16, 2015", W/ English Translation, 21 pgs.
"U.S. Appl. No. 14/358,065, Final Office Action mailed Nov. 18, 2015", 10 pgs.
"U.S. Appl. No. 14/358,065, Response filed Oct. 28, 2015 to Non Final Office Action mailed Jul. 31, 2015", 12 pgs.
"European Application Serial No. 12853965.7, Extended European Search Report mailed Nov. 16, 2015", 10 pgs.
"Japanese Application Serial No. 2015-517243, Final Office Action mailed Dec. 1, 2015", W/ English Translation, 5 pgs.
"U.S. Appl. No. 13/090,036, Notice of Allowance mailed Mar. 19, 2013", 8 pgs.
"U.S. Appl. No. 13/090,036, Notice of Allowance mailed Jul. 15, 2013", 9 pgs.
"U.S. Appl. No. 13/510,825, Response filed Jun. 27, 2013 to Non Final Office Action mailed Mar. 27, 2013", 30 pgs.
"U.S. Appl. No. 13/510,825, Examiner Interview Summary mailed Jul. 10, 2013", 3 pgs.
"U.S. Appl. No. 13/510,825, Final Office Action mailed Aug. 27, 2013", 26 pgs.
"U.S. Appl. No. 13/510,825, Non Final Office Action mailed Mar. 27, 2013", 14 pgs.
"U.S. Appl. No. 13/510,825, Non Final Office Action mailed Jun. 3, 2014", 28 pgs.
"U.S. Appl. No. 13/510,825, Preliminary Amendment filed May 18, 2012", 3 pgs.
"U.S. Appl. No. 13/510,825, Response filed Nov. 26, 2013 to Final Office Action mailed Aug. 27, 2013", 34 pgs.
"U.S. Appl. No. 14/358,065, Preliminary Amendment filed May 14, 2014", 8 pgs.
"U.S. Appl. No. 14/361,094, Preliminary Amendment filed May 28, 2014", 8 pgs.
"Application Serial No. PCT/US2012/065009, Article 19 Amendment filed Mar. 25, 2013", 6 pgs.
"European Application Serial No. 10833722.1, Preliminary Amendment filed Jan. 21, 2013", 21 pgs.
"International Application Serial No. PCT/US2010/046865, International Preliminary Report on Patentability mailed May 30, 2012", 10 pgs.
"International Application Serial No. PCT/US2010/046865, International Search Report mailed Oct. 28, 2010", 2 pgs.
"International Application Serial No. PCT/US2010/046865, Written Opinion mailed Oct. 28, 2010", 8 pgs.
"International Application Serial No. PCT/US2012/065009, Supplemental Article 19 Amendment filed Apr. 26, 2013", 12 pgs.
"International Application Serial No. PCT/US2012/065009, International Preliminary Report on Patentability mailed May 30, 2014", 7 pgs.
"International Application Serial No. PCT/US2012/065009, International Search Report mailed Jan. 25, 2013", 2 pgs.
"International Application Serial No. PCT/US2012/065009, Written Opinion mailed Jan. 25, 2013", 5 pgs.
"International Application Serial No. PCT/US2012/066842, Demand and Response filed Sep. 27, 2013 to Written Opinion mailed Feb. 7, 2013", 25 pgs.
"International Application Serial No. PCT/US2012/066842, International Prelminary Report on Patentability mailed Jun. 12. 2014", 10 pgs.
"International Application Serial No. PCT/US2012/066842, International Preliminary Report on Patentability mailed Dec. 6, 2013", 36 pgs.

(56) References Cited

OTHER PUBLICATIONS

"International Application Serial No. PCT/US2012/066846, Demand and Response filed Sep. 27, 2013 to Written Opinion mailed Feb. 6, 2013", 26 pgs.

"International Application Serial No. PCT/US2012/066846, International Preliminary Report on Patentability mailed Dec. 3, 2013", 16 pgs.

"International Application Serial No. PCT/US2013/031650, International Search Report mailed May 31, 2013", 2 pgs.

"International Application Serial No. PCT/US2013/031650, Written Opinion mailed May 31, 2013", 4 pgs.

"Japanese Application Serial No. 2012-541077, Office Action mailed Mar. 18, 2014", w/English translation, 4 pgs.

Allard, L. F., et al., "A New Paradigm for Ultra-High-Resolution Imaging at Elevated Temperatures", Microscopy and Microanalysis, 14(Supp. S2), (2008), 792-793.

Briceno, M., et al., "In-situ TEM Observations on the Sintering Process of Colloidal Gold Using an Ultra-fast Heating Stage", Microscopy and Microanalysis, 14(Suppl 2), (2008), 1336-1337.

Damiano, John, et al., "A MEMS-based Technology Platform for in-situ TEM Heating Studies", Microscopy and Microanalysis, 14(Suppl), (2008), 1332-1333.

Eakins, D. E., et al., "An in situ TEM study of phase formation in gold-aluminum couples", Journal of Materials Science, 39, (2004), 165-171.

Kamino, T., et al., "A newly developed high resolution hot stage and its application to materials characterization", Microsc. Microanal. Microstruct., 4, (1993), 127-135.

Kamino, T., et al., "In-situ high-resolution electron microscopy study on a surface reconstruction of Au-deposited Si at very high temperatures", Philosophical Magazine A, 75(1), (1997), 105-114.

Min, K.-H., et al., "Crystallization behaviour of ALD-Ta2O5 thin films: the application of in-situ TEM", Philosophical Magazine, 85(18), (Jun. 21, 2005), 2049-2063.

Saka, H., "In situ observation of solid-liquid interfaces by transmission electron microscopy", J. Mater. Res., 20(7), (Jul. 2005), 1629-1640.

Saka, H., "In-situ TEM observation of transformation of dislocations from shuffle to glide sets in Si under supersaturation of interstitials", Philosophical Magazine, 86(29-31), (Oct.-Nov. 2006), 4841-4850.

Tsukimoto, S., et al., "In situ high resolution electron microscopy/electron energy loss spectroscopy oberservation of wetting of a Si surface by molten Al", Journal of Microscopy, 203(Pt 1), (Jul. 2001), 17-21.

Wu, Yiying, et al., "Direct Observation of Vapor—Liquid—Solid Nanowire Growth", J. Am. Chem. Soc., 123, (Mar. 13, 2001), 3165-3166.

"U.S. Appl. No. 14/358,065, Notice of Allowance mailed Jun. 14, 2016", 9 pgs.

"U.S. Appl. No. 14/361,094, Restriction Requirement mailed Aug. 31, 2016", 7 pgs.

"U.S. Appl. No. 14/407,783, Final Office Action mailed Sep. 23, 2016", 8 pgs.

"U.S. Appl. No. 14/407,783, Response filed Sep. 16, 2016 to Non Final Office Action mailed Mar. 16, 2016", 15 pgs.

"Japanese Application Serial No. 2015-202642, Office Action mailed Sep. 6, 2016", (With English Translation), 4 pgs.

"U.S. Appl. No. 13/510,825, Corrected Notice of Allowance mailed Mar. 7, 2016", 2 pgs.

"U.S. Appl. No. 14/358,065, Response filed Feb. 22, 2016 to Final Office Action mailed Nov. 18, 2015", 10 pgs.

"U.S. Appl. No. 14/407,783, Non Final Office Action mailed Mar. 16, 2016", 10 pgs.

"European Application Serial No. 12849761.7, Response filed Feb. 29, 2016 to Extended European Search Report mailed Aug. 7, 2015", 14 pgs.

"European Application Serial No. 13804048.0, Extended European Search Report mailed Feb. 9, 2016", 6 pgs.

"European Application Serial No. 12853965.7, Communication Pursuant to Article 94(3) EPC mailed Oct. 13, 2016", 3 pgs.

"European Application Serial No. 13804048.0, Reponse filed Sep. 7, 2016 to Extended European Search Report mailed Feb. 9, 2016", 39 pgs.

"Japanese Application Serial No. 2014-543623, Office Action mailed Oct. 4, 2016", W/ English Translation, 10 pgs.

"Japanese Application Serial No. 2014-543624, Office Action mailed Oct. 4, 2016", in/ English Translation, with English Translation, 9 pgs.

"U.S. Appl. No. 14/361,094, Non Final Office Action mailed Nov. 15, 2016", 9 pgs.

"U.S. Appl. No. 14/361,094, Response filed Oct. 31, 2016 to Restriction Requirement mailed Aug. 31, 2016", 11 pgs.

"U.S. Appl. No. 14/948,549, Non Final Office Action mailed Oct. 26, 2016", 8 pgs.

"U.S. Appl. No. 14/361,094, Final Office Action mailed Apr. 20, 2017", 7 pgs.

"U.S. Appl. No. 14/361,094, Response filed Apr. 4, 2017 to Non final Office Action mailed Nov. 15, 2016", 20 pgs.

"U.S. Appl. No. 14/407,783, Notice of Allowance mailed Mar. 10, 2017", 6 pgs.

"U.S. Appl. No. 14/407,783, Notice of Allowance mailed Mar. 29, 2017", 6 pgs.

"U.S. Appl. No. 14/407,783, Response filed Feb. 23, 2017 to Final Office Action mailed Sep. 23, 2016", 15 pgs.

"U.S. Appl. No. 14/948,549, Notice of Allowance mailed Mar. 22, 2017", 12 pgs.

"European Application Serial No. 12853899.8, Communication Pursuant to Article 94(3) EPC mailed Mar. 17, 2017", 7 pgs.

"European Application Serial No. 12853899.8, Office Action mailed May 30, 2016", 8 pgs.

"European Application Serial No. 12853899.8, Response filed Dec. 9, 2016 to Office Action mailed May 30, 2016", 15 pgs.

"European Application Serial No. 12853965.7, Response filed Feb. 16, 2017 to Communication Pursuant to Article 94(3) EPC mailed Oct. 13, 2016", 12 pgs.

"European Application Serial No. 12853965.7, Response filed Jun. 8, 2016 to Extended European Search Report mailed Nov. 16, 2015", 17 pgs.

"Japanese Application Serial No. 2014543623, Response filed Mar. 3, 2017 to Office Action mailed Oct. 4, 2016", w/English Translation, 12 pgs.

"Japanese Application Serial No. 2015-202642, Response filed Dec. 5, 2016 to Office Action mailed Sep. 6, 2016", W/ English Claims, 8 pgs.

"Japanese Application Serial No. 2016-074111, Office Action mailed Dec. 12, 2016", w/English Translation, 6 pgs.

"U.S. Appl. No. 14/361,094, Examiner Interview Summary dated Jul. 26, 2017", 3 pages.

"U.S. Appl. No. 14/361,094, Non Final Office Action dated Jul. 31, 2017", 4 pages.

"U.S. Appl. No. 14/361,094, Response filed Jul. 20, 2017 to Final Office Action dated Apr. 20, 2017", 13 pages.

"U.S. Appl. No. 14/407,783, Notice of Allowance dated Jul. 21, 2017", 5 pages.

"U.S. Appl. No. 14/948,549, PTO Response to Rule 312 Communication dated Aug. 14, 2017", 2 pages.

"Japanese Application Serial No. 2014-543623, Examiners Decision of Final Refusal dated Aug. 22, 2017", Without English Translation, 3 pages.

"Japanese Application Serial No. 2014-543624, Examiners Decision of Final Refusal dated Aug. 22, 2017", 3 pages.

"Japanese Application Serial No. 2016-074111, Response filed Aug. 1, 2017 to Office Action dated Dec. 12, 2016", 20 pages.

HIGH TEMPERATURE HEATING SYSTEM

CLAIM OF PRIORITY

This patent application is a U.S. National Stage Filing under 35 U.S.C. 371 from International Patent Application Serial No. PCT/US2012/066842, filed Nov. 28, 2012, published on Jun. 6, 2013 as WO 2013/082145 A1, which claims the benefit of priority of U.S. Provisional Patent Application Ser. No. 61/564,188, filed on Nov. 28, 2011 all of which are hereby incorporated by reference herein in their entirety.

STATEMENT REGARDING FEDERALLY SPONSORED RESEARCH OR DEVELOPMENT

This invention was made with Government support under (FA8650-11-M-5178) awarded by the United States Air Force. The Government has certain rights in this invention

TECHNICAL FIELD

This document pertains generally, but not by way of limitation, to mechanical testing and heating of samples at scales of microns and smaller.

BACKGROUND

Indentation, scratch, tensile and compression testing at scales of microns or less are methods for quantitatively measuring mechanical properties, such as elastic modulus and hardness, of materials. For instance, probes capable of determining loading forces and displacement are used. In some examples, forces applied in mechanical testing at scales of microns or less are less than 10 N, with a typical displacement range being smaller than 500 µm, and with a noise level typically being better than 10 nm root mean square (rms). Force and displacement data measured with the probe are used to determine the mechanical properties of the sample and one or more of the elastic or plastic characteristics and the associated material phase changes. In one example, for sample property estimation a micro/nano-indenter is integrated with a characterized indenter tip having a known geometry and known mechanical properties.

Some of the emerging mechanical characterization techniques at scales of microns or less include, but are not limited to, quantitative transmission electron microscopy (TEM) and scanning electron microscopy (SEM) in-situ mechanical testing (as well as optical microscope techniques in some instances). These in-situ mechanical testing techniques enable monitoring of the deformation of a sample in real time while measuring the quantitative mechanical data. Coupling a mechanical testing system configured for testing at scales of microns or less with electron or optical microscopy imaging allows researchers to study structure property correlation and the influence of pre-existing defects on the mechanical response of materials. In addition to imaging, selected-area diffraction can be used to determine sample orientation and loading direction influence on mechanical response. Moreover, with in-situ electron or optical microscopy mechanical testing, the deformation can be viewed in real-time rather than "post-mortem". Performing in-situ mechanical testing at scales of microns or less can provide unambiguous differentiation between the many possible causes of force or displacement transients which may include dislocation bursts, phase transformations, shear banding or fracture onset. Mechanical testing at micron or nano scales with elevated temperature is an important part of material characterization for materials having phase changes or variant mechanical properties as temperature increases. Many materials and devices are designed to perform at temperatures other than room temperature. The thermo-mechanical reliability of advanced materials needs to be fully understood through proper material testing. Due to this reason, it is often preferred to test the mechanical properties of these materials at their operating temperatures. The measured data at the elevated temperature can be used to estimate the performance of the materials in their normal operating environment. For example, understanding the thermo-mechanical response of polymer composites designed for enhanced mechanical properties will result in lighter and stronger materials for the aerospace and automobile industries, improving efficiency in the transportation sector and energy savings. Understanding the fundamentals of strengthening mechanisms in ceramic matrix composite materials will help to improve the lifetime usage of these materials in real world applications. To improve the efficiency of turbine powered jet engines, new turbines must run hotter with less cooling. Understanding the mechanical properties at elevated temperature of individual components such as disks, blades and nozzles is critical for the aerospace industry.

OVERVIEW

The present inventors have recognized, among other things, that a problem to be solved can include consistent heating of a relatively large sample having a planar configuration and multiple testing locations spread over the plane of the sample. Additionally, the present inventors have recognized that heating to temperatures greater than 400 degrees Celsius, and in some cases greater than 1100 degrees Celsius is difficult in light of issues of thermal-mechanical drift, expansion of components to a heater, and consistent heating of a planar sample. In one example, the stage heater described herein and a testing assembly including the stage heater provides solutions to these problems. The stage heater provides a stage plane having an expansive surface configured to receive samples having a variety of configurations thereon (e.g., planar, non-planar, irregular, linear, non-linear samples or the like). The stage heating element is distributed across the stage plane (e.g., an opposed surface of the stage plane to the surface that receives a sample) and accordingly is configured to heat substantially the entire stage plane. Optionally, the stage heating element extends between first and second stage edges and first and second stage ends to provide consistent and reliable heating across the stage plane. During a testing procedure, the sample overlying the stage plane is heated to a desired temperature consistently across the sample by way of the distributed stage heating element covering the stage plane. For instance, with a planar sample, the surface to surface contact with the stage plane transmits heat consistently from across the stage plane to the sample. In another example, where the sample has an irregular configuration (e.g., non-planar), the distributed character of the heating to the stage plane heats the sample at each point of contact along the stage plane to substantially the same temperature. Stated another way, the stage heater is able to provide consistent heating across the stage plane to non-planar samples coupled along the stage plane.

Additionally, the materials and configuration of the stage heater allow the stage heater to reliably heat samples positioned on the sample plane to temperatures of greater than 400 degrees Celsius (e.g., 500 or 750 degrees Celsius or greater). In another example, the materials and configuration of the stage heater allow the stage heater to reliably heat samples to temperatures of 1100 degrees Celsius or greater (e.g., 1500 Celsius or greater). Additionally, the stage heater described herein localizes heating of the sample plane and accordingly throttles heat transfer to stage mounts coupled with other features of the testing assembly, such as a multiple degree of freedom stage. By throttling heat transfer in this manner the stage heater is able to rapidly heat a sample to the desired temperature without requiring a large energy output otherwise necessary if other components of the testing assembly (having larger thermal masses) were heated by the stage heater. The stage heater throttles heat transfer by localizing the stage heating element to the region of the stage plane, and isolating the stage plane from the remainder of the stage heater including two or more support mounts. In one example two or more bridges having a small cross sectional area in a direction orthogonal to heat transfer from the stage plane extend between the stage plane and the two or more support mounts. Optionally, the two or more bridges each include a plurality of bridges with voids therebetween that cooperate with the bridges to isolate the stage plane from the two or more support mounts. Further, the materials of the stage heater are chosen to provide the heater with a low thermal conductivity (at least around 10 W/m·K or lower), a low coefficient of thermal expansion (at least around 20 µm/m or lower), along with a high elastic modulus (at least around 50 GPa or higher). A high elastic modulus provides rigid support to the sample during mechanical testing.

Further still, the optional probe heater is integrated with the heating system to substantially prevent a sample temperature drop that otherwise occurs when an unheated tip contacts the sample. By heating the probe to substantially the same temperature as the sample, the sample is maintained at the desired testing temperature during high temperature mechanical testing. Accordingly, a testing assembly including the heating system (the stage heater and the probe heater) provides accurate and reliable determinations of the mechanical characteristics of the sample at the desired elevated temperatures.

Moreover, the present inventors have recognized, among other things, that a problem to be solved can include consistent heating of a relatively large samples (planar, non-planar and the like) while at the same time providing a stiff underlying stage structure at each test location of the sample distributed across the sample plane. In one example, the stage heater described herein and the testing assembly (including the stage heater) address this problem by providing a stage plane of the stage heater that is supported at two or more support mounts on opposing sides of the stage plane. Two or more bridges couple the stage plane with the two or more stage mounts and accordingly hold the stage plane statically. Optionally, the two or more bridges include a plurality of bridges spaced around the stage plane that provide three or more points of contact between the stage plane and the two or more stage mounts. The support provided by the plurality of bridges provides robust support to the stage plane and minimizes tilting of the stage plane during mechanical testing.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
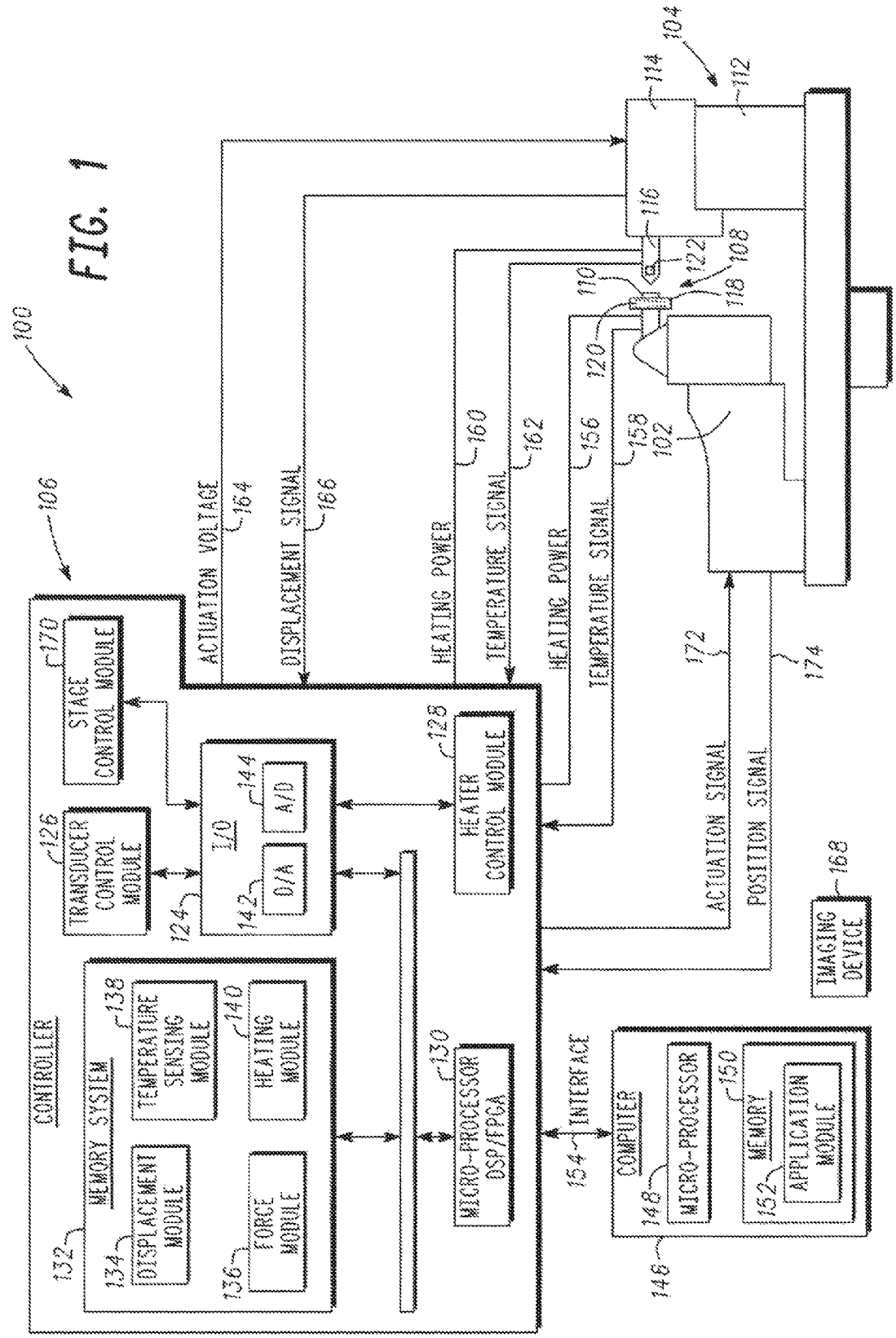
FIG. 1 is a block diagram of one example of a nano-mechanical test system.

According to embodiments described herein, a system and method are provided for mechanically testing samples at the nano and micro scales (i.e., scales of microns or less), including, but not limited to, nanostructures, thin films and the like. Such testing is performed, in one example, to determine the mechanical properties of the materials composing the subjects. According to one embodiment, as will be described in greater detail herein, the testing assembly described herein includes a heating system including stage based and optional probe based heaters having heating and sensing elements in the sample stage or the probe assembly (e.g., at a probe tip). The heater enables the use of instruments that provide precise actuation forces, corresponding indenting or other deformation (e.g., indentation, scratching, tension, compression and the like), and high resolution displacement sensing on at least scale of microns or less (nanometers or micrometers).

A testing assembly and heating system usable with the testing assembly are described herein. In one example, a stage heater is provided for heating a relatively large sample having an optional planar configuration and multiple testing locations spread over the plane of the sample. The stage heater described herein is configured to reliably heat the entire planar sample to temperatures greater than 400 degrees Celsius, and in some cases greater than 1100 degrees Celsius while at the same time minimizing thermal expansion and thermal-mechanical drift of one or more of a stage or adaptor coupled with the stage heater. The stage heater provides a stage plane having an expansive surface configured to receive samples of various sizes and shapes thereon.

The stage heating element is distributed across the stage plane (e.g., an opposed surface of the stage plane to the surface that receives a sample) and accordingly is configured to heat substantially the entire stage plane. Optionally, the stage heating element extends between first and second stage edges and first and second stage ends to provide consistent and reliable heating across the stage plane. During a testing procedure, the sample overlying the stage plane is heated to a desired temperature consistently across the sample by way of the distributed stage heating element covering the stage plane.

Additionally, the stage heater with the stage plane including the distributed heating is adapted for heating samples having other configurations (e.g., non-planar, irregular, linear, non-linear or the like). These samples are coupled and retained along the stage plane with any one of the retention features described herein including, but not limited to, adhesives, fasteners, clamps, welds and the like. Accordingly the stage heater described herein is similarly configured to heat samples having a non-planar configuration. The distributed heating provided by the stage heating element across the stage plane ensures that a sample, including a non-planar sample with two or more points of contact with the stage plane, is heated to the same temperature at every point of contact of the sample with the stage plane.

Additionally, the materials and configuration of the stage heater allow the stage heater to reliably heat samples positioned on the sample plane to temperatures of greater than 400 degrees Celsius. In another example, the materials and configuration of the stage heater allow the stage heater to reliably heat samples to temperatures of 1100 degrees Celsius or greater. Further, the stage heater described herein localizes heating of the sample plane and accordingly throttles heat transfer to stage mounts coupled with other features of the testing assembly, such as a multiple degree of freedom stage. By throttling heat transfer in this manner the stage heater is able to rapidly heat a sample to the desired temperature without requiring a large energy output otherwise necessary if other components of the testing assembly (having larger thermal masses) were heated by the stage heater. The stage heater throttles heat transfer by localizing the stage heating element to the region of the stage plane, and isolating the stage plane from the remainder of the stage heater including two or more support mounts. In one example two or more bridges extend between the stage plane and two or more support mounts for the stage heater. Optionally, the two or more bridges each include a plurality of bridges with voids therebetween that cooperate with the bridges to thermally isolate the stage plane from the two or more support mounts. Further, the materials of the stage heater are chosen to provide the heater with a low thermal conductivity (at least around 10 W/m·K or lower), a low coefficient of thermal expansion (at least around 20 µm/m or lower), along with a high elastic modulus (at least around 50 GPa or higher). A high elastic modulus provides rigid support to the sample during mechanical testing.

Further still, the optional probe heater is integrated with the heating system to substantially prevent a sample temperature drop that otherwise occurs when an unheated tip contacts the sample. By heating the probe to substantially the same temperature as the sample, the sample is maintained at the desired testing temperature during high temperature mechanical testing. Optionally, the probe heater includes a configuration similar in at least some regards to the stage heater. For instance, the probe heater includes materials and construction that throttle heat transfer from the probe to proximal portions of the probe and a transducer coupled with the probe. In still other examples, the probe heater includes support columns and voids that cooperate with the materials of the probe heater to substantially minimize heat transfer (and corresponding thermal expansion and thermal-mechanical drift) into proximal portions of the probe and the transducer having greater thermal masses.

Accordingly, a testing assembly including the heating system (the stage heater and the probe heater) as described herein provides accurate and reliable determinations of the mechanical characteristics of the sample at desired elevated temperatures.

FIG. 1 is a schematic block diagram illustrating an example of a testing assembly 100 including a stage 102, a transducer assembly 104 and a controller 106. The testing assembly 100 employs a heating system 108 for heating and sensing the temperature of a test sample 110. In one example, the transducer assembly 104 includes a flexural actuator 112 and a transducer 114, such as a multi-plate capacitor electro-mechanical transducer having a displaceable probe 116. The transducer includes, but is not limited to, indentation, compression, tensile, fatigue, tribology, fracture instruments and the like.

The testing assembly 100 further includes a stage 102, as described above. In one example, the stage 102 includes a multiple degree of freedom stage having one or more actuators configured to move a stage surface 118 according to two or more degrees of freedom. As will be described herein, one example of a multiple degree of freedom stage includes a stage having translational, rotational and tilting degrees of freedom. According to one example, the heating system 108 is configured for coupling with the stage 104 and the transducer by way of a stage heater 120 and a probe heater 122, described in further detail below. The multiple degree of freedom stage described herein is one example of a system that would benefit from the heating system 108. Additionally, the heating system 108 described herein is also configured for use with any mechanical, electro-mechanical or electrical testing assembly or instrument that would benefit from one or more of a heated sample or probe.

According to one embodiment, the controller 106 includes an input/output module 124, a transducer control module 126, a heater control module 128, a processor 130, such as microprocessor or digital signal processor (DSP) and/or field programmable gate array (FPGA), for example, and a memory system 132. According to one embodiment, the memory system 132 includes a displacement module 134, a force module 136, a temperature sensing module 138, and a heating module 140. According to another embodiment, the input/output module 124 further includes a D/A converter 142, and an A/D converter 144.

In one example, the computer 146 includes a processor 148 and a memory system 150 that stores an application module 152. The computer 146 may access and communicate with the controller 106 via an interface 154 (e.g. a USB interface). FIG. 1 shows the computer 146 and controller 106 as separate entities. In other examples, the computer 146 and the controller 106 are combined as part of a single processing and control system.

According to one embodiment, the application module 152, displacement module 134, and force module 136 each include instructions respectively stored in memories 132 and 150 and which are accessible and executable by the processor 130. The controller 106 is configured to control and monitor the movement of displaceable probe 116 (through one or more of the flexural actuator 112 or the transducer 114) and to provide data representative of a displacement of the displaceable probe 116 to the computer 146 through the interface 154. According to one embodiment, the controller 106 is configured to determine and adjust a force applied to the test sample 110 by the displaceable probe 116.

Additionally, the controller 106 is configured to control and monitor the temperature of the heating system 108 (including the stage heater 120 and the probe heater 122) and the sample 110 and to provide data representative of a temperature of the heating system 108 and the sample 110 to the computer 146 via interface 154. In one example, the controller 106 is configured to determine and adjust a heating power 156 applied to the heating system 108 and the sample 110 to achieve a desired sample temperature (and heater 120 temperature) for testing and observation of the sample. In one example, the controller 106 (e.g., the heater control module 128) uses the temperature signal 158 to adjust the heater power 156 to achieve the desired test subject temperature through one or more control methods including closed loop feedback control. In a similar manner, the heater power 160 for the probe heater 122 is adjusted by the heater control module 128 according to the temperature signal 162 provided from the probe heater. Optionally, the heater control module 128 ensures the heating system 108 including the stage heater 120 and the probe heater 122 are operated cooperatively to achieve the same temperature at the displaceable probe 116 and the stage surface 118. That is to say, one or more of the stage surface 118 and the probe heater 122 are actively heated to avoid passive unpredictable heating of a sample through heat transfer between the sample and the probe. Accordingly, there is minimal heat transfer through the sample 110 (e.g., between the stage surface 118 and the probe 116) as the heated probe 116 contacts the heated sample 110 positioned on the stage surface 118. By heating both the probe 116 and the stage surface 118, the heating system 108 is able to consistently and reliably test a sample 110 with the test assembly 100 without adversely altering the characteristics of the sample through unpredictable heat transfer caused by unheated components (e.g., the probe or the stage) in contact with the sample 110. Instead, the sample temperature and the probe temperature are adjusted through operation of the heating system 108 (controlled by the heater control module 128) to ensure the probe 116 is substantially the same temperature as the sample 110 at contact and throughout the testing procedure by way of active heating.

In operation, a user can program the controller 106 with the computer 146 through the application module 152. According to one embodiment, the controller 106, through the force module 136, provides an input or force signal to the transducer assembly 104 representative of a desired force for application to the test sample 110 by the displaceable probe 116. In response to the input actuation force signal, the transducer assembly 104 (one or more of the flexural transducer or the transducer) drives the displaceable probe 116 toward the sample 110. The displaceable probe 116 contacts and applies the desired force to the test subject 110. As will be described herein, displacement sensors are included in one or more of the transducer 114 and the flexural actuator 112. Optionally, the displacement sensor includes a transducer (e.g. a capacitive transducer) configured to detect movement of the displaceable probe 116 along at least one axis, and provides a displacement signal 166 to the controller 106 representing measurement of the movement of the displaceable probe 116. In other embodiments, in addition to movement along a single axis, the displacement sensors of one or more of the transducer 114 and the flexural actuator 112 detect and measure movement of the displaceable probe 116, such as displacement along one or more of the x, y or z axes or rotational movement about one or more of these axes. According to one embodiment, the testing assembly 100 further includes an imaging device 168 comprising an instrument such as an electron microscope, an optical microscope, or a scanning probe microscope (SPM) (e.g., an atomic force microscope (AFM)) configured to provide images of the sample 110 mounted to stage surface 118, including one or more of images and video of the sample before, during and after mechanical testing such as indentation, compression, fatigue and fracture testing and the like.

For instance, test systems suitable for configuration with the heating system 108 include, but are not limited to, optical microscopes, scanning probe microscopes (SPM), electron microscopes and the like. In each of these examples, ex-situ or in-situ heating is performed with the heating system 108. Another test system suitable for configuration with the heating system 108 is an electron microscope (e.g. one or more of transmission electron microscope (TEM) or scanning electron microscope (SEM)) in-situ nanomechanical tester commercially available under the trade name PicoIndenter from Hysitron, Incorporated, of Eden Prairie, Minn., USA.

During a temperature controlled mechanical test, as will be described in greater detail below, the heating system 108 is controlled so as to heat and maintain the sample 110 at the desired temperature. The heating system 108 is operated with at least one of open loop control or closed loop control. For more accurate temperature regulation in a changing thermal environment, a closed loop control system utilizing the temperature signals 158, 162 as feedback are used. When the sample 110 temperature and the probe 116 temperature reach the desired temperature, the transducer assembly 104 is operated to apply a force with the moveable probe 116 to the sample 110. According to one embodiment, the temperature of the sample 110 is measured by the heating system 108 and the force applied and a displacement of the indented material of the sample 110 are measured by the testing assembly 100, as described herein. The force and displacement data and images of the corresponding deformation are substantially simultaneously measured in real-time and observed by a combination of the transducer assembly 104 (e.g. one or more displacements sensors) and the imaging device 168 (e.g., an electron microscope). Stated another way, examination of the test subject—through the above described measuring and imaging techniques—at a specified testing temperature is performed without any appreciable pause between deformation and measurement, imaging or heating. Observation and determination of these parameters and phenomena at or immediately after indentation are sometimes critical in the accurate assessment and determination of corresponding material properties.

Referring again to FIG. 1, the stage 102 is shown positioned relative to the displaceable probe 116. In one example, and as previously described herein the stage 102 includes a multiple degree of freedom stage having two or more degrees of freedom to position the stage surface 118 with the sample 110 thereon relative to the displaceable probe 116. In one example, the testing assembly is used in a larger overall instrument assembly, such as a scanning electron microscope (transmission electron microscope with adaptation of the assembly 100) or optical microscope. The positioning of the stage surface 118 relative to the displaceable probe 116 allows for a variety of instruments of a larger overall instrument assembly to have access to the sample 110 while the sample is tested with the displaceable probe 116. Additionally, the orientation of the stage surface 118 for instance by operation of two or more degrees of freedom of the stage 102 allows for testing of the sample 110 from a number of angles and orientations to thereby allow for scratching, indentation, angled indentation testing and the like.

As shown in FIG. 1, the controller 106 includes a stage control module 170. In one example, the stage control module 170 is configured to provide an actuation signal 172 to the stage 102. The actuation signal 172, in one example, includes one or more component signals therein configured to operate the various stages of the stage 102. For instance, in one example, the stage 102 includes one or more of linear (translational), rotational and tilting stages. The actuation signal 172 accordingly has one or more components therein configured to operate each of the stages. In one example, the stage control module 170 provides instructions by way of the actuation signal 172 to the stage 102 according to a desired orientation input into the controller 106, for instance, by way of the computer 146. For a particular testing scheme the stage control module 170 moves the stage surface 118 into a desired orientation (or orientations) to allow for access of the displaceable prove 116 to the sample 110 according to that desired orientation. In another example, the stage control module 170 allows for positioning and repositioning of the sample 110 for testing at multiple locations of the sample 110. For instance, where a plurality of test locations are distributed across the sample 110 the stage 102 having a plurality of degrees of freedom is able to move the sample 110 and the stage surface 118 into those orientations necessary for the displaceable probe 116 to have access to the testing locations.

As the stage 102 moves into the desired orientation according to the actuation signal 172, a position signal 174 for instance provided by one or more of encoders, potentiometers and other detection devices, is submitted to the controller 106 (e.g., the stage control module 170). In one example, the stage control module 170 is configured to index the position of the various stages of the stage 102 according to these position signals 174. For instance, in one example, the stage control module 170 uses a closed loop control system using the position signal 174 as feedback to ensure accurate and reliable positioning of the stage surface 118 according to operation of the stage 102. The multiple degree of freedom stage described herein is one example of a system that would benefit from the heating system 108. Additionally, the heating system 108 described herein is also configured for use with any mechanical, electro-mechanical or electrical based testing assembly or instrument that would benefit from one or more of a heated sample or probe.

For instance, for electrical, electro-mechanical, thermoelectrical, or thermo-electro-mechanical testing (e.g., electrical based testing), a voltage or current is applied through the probe and the sample and the resistance or capacitance change of the sample or probe-sample contact area is measured, for instance with an electrical characteristic module of the controller 106 (e.g., within the memory system 132). In another example, electrical, electro-mechanical, thermo-electrical, or thermo-electro-mechanical testing is conducted with sample electrically connected (e.g., by way of voltage or current application) to measure the resistance or capacitance change while the sample is heated, mechanically stressed or both. With this measurement scheme only the sample is connected to the source of electricity and only the sample is measured. The probe 116 may optionally provide mechanical pressure (or force) to the sample but is not used to measure the electrical properties of the sample. In another example, the probe 116 also conducts mechanical testing during the electrical based testing. As described herein (see FIGS. 6 and 9) the electrical wire connections for the testing methods described above can use either 2 point probe measurement or 4-point probe measurement.

Figure 2:
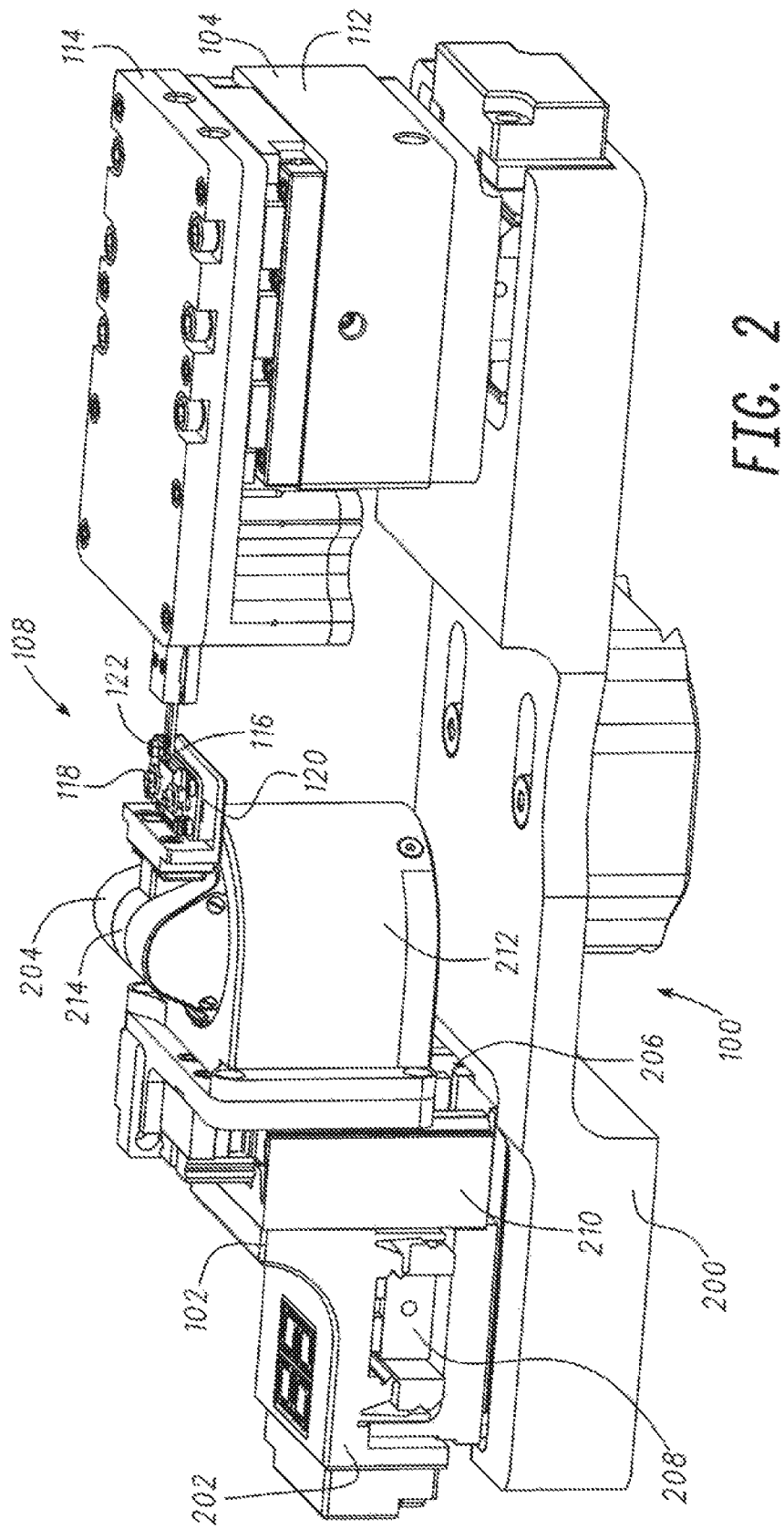
FIG. 2 is a perspective view of one example of a testing assembly including a stage heater and a probe heater.

FIG. 2 shows a perspective view of the testing assembly 100. As previously described, the testing assembly 100 includes a stage 102 and a transducer assembly 104. In the examples shown in FIG. 2, the stage 102 and the transducer assembly 104 are coupled with an assembly mount 200. The assembly mount 200 is configured in at least some examples to couple with a larger instrument assembly, for instance, the stage surface of one or more of a scanning electron microscope, an optical microscope or another instrument.

As shown in FIG. 2, the transducer 104 has a flexural actuator 112 coupled with a transducer 114. As will be described in further detail herein the displaceable probe 116 is coupled with the transducer 114 and the transducer 114 is in turn coupled with the flexural actuator 112. Movement of the displaceable probe 116, for instance, to scratch across or indent the tip within a sample is provided by one or more of the flexural actuator 112 and the transducer 114. In one example, the flexural actuator 112 is used to provide the displacement movement of the displaceable probe 116 while the transducer 114 is used to measure the corresponding movement of the displaceable probe 116 and forces incident upon the sample by way of engagement between the probe 116 and the sample during a testing procedure. That is to say, in at least one example the flexural actuator 112 provides the movement of the displaceable probe 116 while the transducer 114 measures the movement and forces incidence on the probe 116.

Referring again to FIG. 2, the stage 102 is shown having a plurality of degrees of freedom. For instance, the stage 102 includes in one example a linear stage assembly 202 coupled with an assembly mount 200. Optionally, the transducer assembly 104 is also coupled with the assembly mount 200. In another example, the stage 102 includes a rotation and tilt stage assembly 204 coupled in series with the linear stage assembly 202. As described herein, the stage 102 has in one example two or more degrees of freedom to allow for positioning of the stage surface 118 relative to the displaceable probe 116. For instance, the linear stage assembly 102 includes first, second and third linear stages 206, 208, 210. The first, second and third linear stages 206, 208, 210 in one example correspond to the three Cartesian axes X, Y and Z. For instance, the first linear stage 206 corresponds to the Y axis, the second linear stage 208 corresponds to the X axis and the third linear stage 210 corresponds to the Z axis.

As further shown in FIG. 2, the rotation and tilt stage assembly 204 includes a corresponding rotational stage 212 coupled with a tilt stage 214. The stage surface 118 is coupled with the tilt stage 214, for instance, by a spindle assembly rotatably coupled with the remainder of the tilt stage 214. Coupling of the stage surface 118 with the stage 102 allows for the positioning of the stage surface 118 and a sample thereon in any number of discrete orientations relative to the displaceable probe 116.

Additionally, and as will be described in further detail herein the heating system 108 is coupled with each of the displaceable probe 116 and the stage surface 118 in one example. For instance, the heating system 108 includes the stage heater 120 localized to the stage surface 118 and the probe heater 122 is localized to the displaceable probe 116 for instance adjacent to a tip of the displaceable probe 116. The localized positioning and isolation of the heating system 108 including the component stage heater 120 and the probe heater 122 allows for the rapid heating of a sample positioned on the stage surface 118 while at the same time allowing for mechanical testing of the sample without heat transfer between the heated sample and the heated displaceable probe 116. As further described herein, in one example the stage heater 120 provides the stage surface 118 by way of a stage plane 306.

Figure 3A:
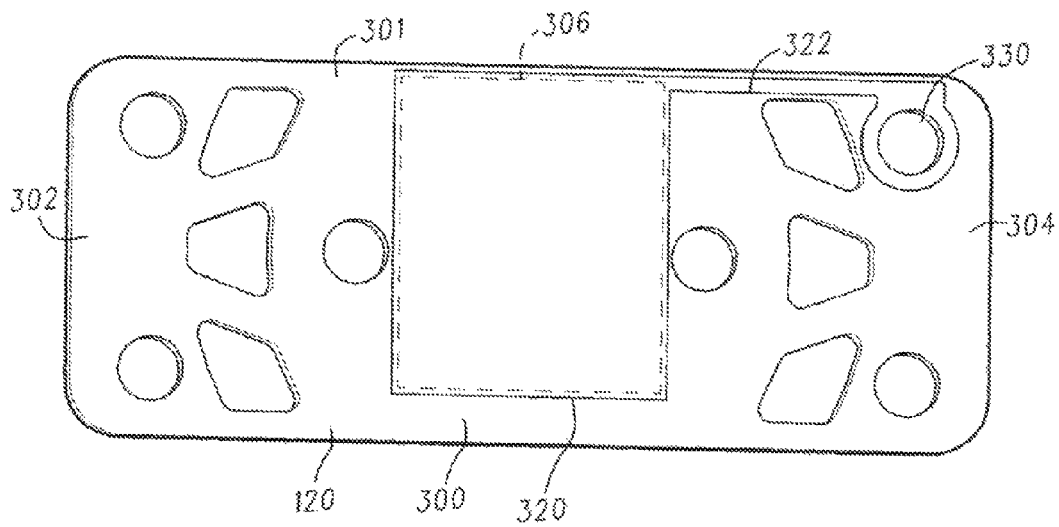
FIG. 3A is a perspective view of a first face of a stage heater.
Figure 3B:
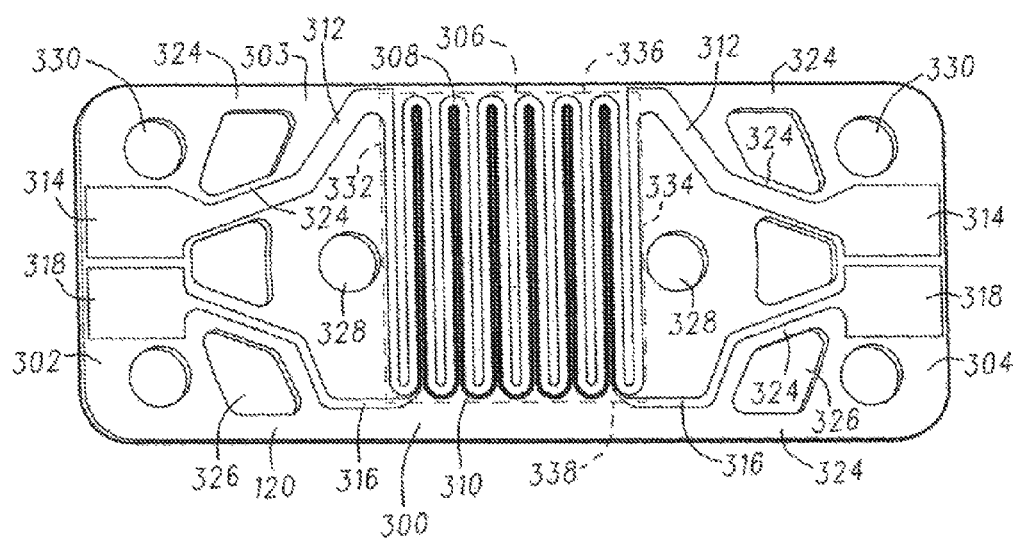
FIG. 3B is a perspective view of a second face of the stage heater of FIG. 3A.

FIGS. 3A and 3B show one example of a stage heater 120. Referring first to FIG. 3A, the stage heater 120 includes a heater body panel 300 including a substrate upon which the remainder of the stage heater 120 is formed or coupled with. In one example, the heater body panel 300 extends between first and second support mounts 302, 304, for instance at opposed ends of the body panel.

The stage heater 120 has a substantially planar configuration between the first and second support mounts 302, 304 with the stage plane 306 positioned between the first and second support mounts 302, 304 along the heater body panel 300. The stage plane 306 is shown in dashed lines in FIG. 3A, and is the portion of the stage heater 120 sized and shaped for reception of samples, such as the sample 110 shown in FIG. 1. As will be described herein, the stage plane 306 has the distributed planar configuration shown in FIG. 3A to accordingly receive and retain a sample having a distributed surface area optionally with a corresponding plurality of testing locations distributed over the sample.

In another example, the stage heater 120 shown in FIG. 3A has a first face 301 directed toward the displaceable probe 116 shown in FIG. 2. The stage plane 306 is provided along the first face 301. The first face 301 includes an electron discharge film 320 substantially coextensive with the stage plane 306. The electron discharge film 320 is configured to discharge electrons built up on the sample for instance during scanning electron microscopy. As shown, the electron discharge film 320 is coupled with a discharge trace 322 extending for instance to one or more of the heater mount orifices 330 further described herein. In one example, the electron discharge film 320 is coupled with a conductive contact for instance a fastener or the like received through the heater mount orifice 320 to thereby allow for the discharge of electrons built up on the electron discharge film 320.

Referring now to FIG. 3B, a second face 303 (opposed to the first face 301) of the stage heater 120 is shown. The second face is directed toward the stage 102 or an adaptor coupled with the stage 102 when stage heater 120 is installed as shown in FIG. 2. The stage heater 120 includes a stage heating element 308 distributed across the stage plane 306 (e.g., along the surface of the second face 303 underlying the stage plane). As will be described herein, the distributed configuration of the stage heating element 308 across the stage plane allows for the consistent and reliable heating of the entirety of the stage plane 306. That is to say, a sample positioned on the stage plane 306 (e.g. the first face 301 of the stage heater 120) is consistently and reliably heated to the same temperature across the entirety of the sample because of the distributed configuration of the stage heating element 308 relative to the stage plane 306 (the stage plane 306 is shown in dashed lines in FIG. 3B).

As shown in the example, the stage heating element 308 optionally has a wide configuration on each of the serpentine passes of the element to facilitate coverage of the stage heating element 308 over a large portion of the stage plane 306. The temperature sensing element 310 is also distributed across the stage plane 306. In the example shown in FIG. 3B, the temperature sensing element 310 has a smaller width relative to the width of the stage heating element 308. The temperature sensing element extends in a serpentine fashion similar to that of the stage heating element 308 and allows for reliable temperature measurements of the entirety of the stage plane 306. In one example, the stage heating element 308 extends over a substantial portion of the stage plane 306. Optionally the stage heating element 308 extends between at least a first stage plane edge 332 and a second stage plane edge 334 as well as between first and second stage plane ends 336, 338 of the stage plane 306. Accordingly, the stage heating element 308 covers substantially the entire surface of the stage plane 306 to ensure reliable and consistent heating of the stage plane.

As further shown in FIG. 3B, the stage heating element 308 is coupled with heating leads 312 extending away from the stage heating element 308, for instance across one or more bridges 324 described herein below. The heating leads 312 are further coupled with heating contacts 314 adjacent to the first and second support mounts 302, 304. In a similar manner, sensing leads 316 extend from the temperature sensing element 310 across the bridges 324 to sensing contacts 318. In one example, upon mounting of the first and second support mounts 302, 304, for instance with corresponding portions of the stage 102 shown in FIGS. 1 and 2, the heating contacts 314 and the sensing contacts 318 are automatically coupled with corresponding contacts of the stage 102 including, but limited to, pogo pins, displaceable contacts, static contacts or the like. The stage heater 120 is thereby able to automatically electrically couple with corresponding contacts of the stage 102 to ensure heating and sensing of the temperature of the stage plane 306 upon installation. Optionally, other instruments that would benefit from the stage heater 120 includes similar contacts sized and shaped for automatic electrical coupling with the heating and sensing contacts 314, 318 upon installation of the stage heater 120.

Referring again to FIG. 3B, the stage plane 306 is isolated from the remainder of the stage heater, for instance, the first and second support mounts 302, 304 by way of one or more bridges 324 extending between the support mounts and the stage plane 306. The bridges 324 are optionally formed in the heater body panel 300. That is to say the heater body panel 300 is a unitary substrate including the mounts 302, 304, the bridges 324 and the portion of the panel including the stage plane 306. The bridges 324 provide heat throttling features having a small cross-sectional surface area relative to a direction of heat flow from the stage plane 306 to the remainder of the stage heater 120 (e.g., the first and second support mounts) and substantially throttle heat transfer from the stage heating element 308 to other portions of the stage heater 120 including portions of the stage heater coupled with the stage 102. The bridges 324 substantially constrain heating to the stage plane 306 without significant heating of the first and second support mounts 302, 304 and corresponding heating of portions of the stage 102 coupled with the stage heater 120.

In another example, pluralities of bridges 324 are provided at one or more of the edges of the stage plane 306. For instance, as shown in FIG. 3B, four separate bridges 324 are provided between the first support mount 302 and the stage plane 306. Similarly, in the example shown in FIG. 3B, four bridges 324 are provided between the second support mount 304 and the stage plane 306. The plurality of bridges 324 include voids 326 formed between the bridges (or to the sides of the bridges). The voids 326 cooperate with the bridges to provide a conductive void (and convective voice in a vacuum environment) between the stage plane 306 and the first and second support mounts 302, 304.

Additionally, by providing a plurality of bridges 324, for instance three or more bridges between the first and second support mounts 302, 304 and the stage plane 306, at least three point supportive contact is provided for the stage plane 306. Because samples are optionally distributed across the stage plane 306 (e.g., along x and y axes) in at least one example, mechanical testing at a variety of locations over the stage plane 306 provides moments to the stage heater 120. The three point supportive contact provided by the bridges 324 between the stage plane 306 and the first and second support mounts 302, 304 provides robust mechanical support to the stage plane 306 and substantial resistance to twisting or tilting of the stage plane 306 caused by mechanical engagement by the displaceable probe 116. That is to say, a sample positioned over the stage plane 306 is robustly statically held in place during mechanical testing, for instance with engagement of the displaceable probe 116. Optionally, the provision of supplemental bridges 324, such as the plurality of bridges shown in FIG. 3B, provides enhanced structural support to the stage plane 306 and accordingly further prevents tilting or twisting of the stage plane 306, for instance with mechanical engagement of the displaceable probe at positions anywhere along the stage plane 306 and irrespective of whether the displaceable probe applies compressive, tensile or lateral forces to a sample on the stage plane 306.

Referring again to FIGS. 3A and 3B, the stage heater 120 includes optional sample mounting orifices 328. The sample mounting orifices 328 work in cooperation with one or more fasteners coupled with the sample positioned over the stage plane 306 to hold the sample on the stage plane 306. Fastening of the sample to the stage plane 306 (e.g., with fasteners, clamps, adhesives, welds and the like) ensures the stage plane 306 (heated by the stage heating element 308) is intimately engaged in surface to surface contact with the sample and accordingly able to consistently and reliably heat the entirety of the sample positioned thereon. In other examples, the stage heater 120 includes other fastening mechanisms including but not limited to, adhesives, mechanical couplings, interference fits, welds and the like configured to hold or retain a sample in surface to surface contact with the stage plane 306. In another example, the stage heater 120 includes a plurality of heater mounting orifices 330 positioned at either side of the first and second support mounts 302, 304. The heater mounting orifices 330 allow for the coupling of the stage heater 120 with another assembly, for instance with portions of an adaptor or a stage coupled with an adaptor such as the stage 102 shown in FIG. 2. Optionally, the stage heater 120 includes other fastening means for coupling of the heater with another instrument (e.g., a stage, instrument housing or the like) including, but not limited to, clamping features, mechanical couplings, adhesives, welds and the like.

Figure 4:
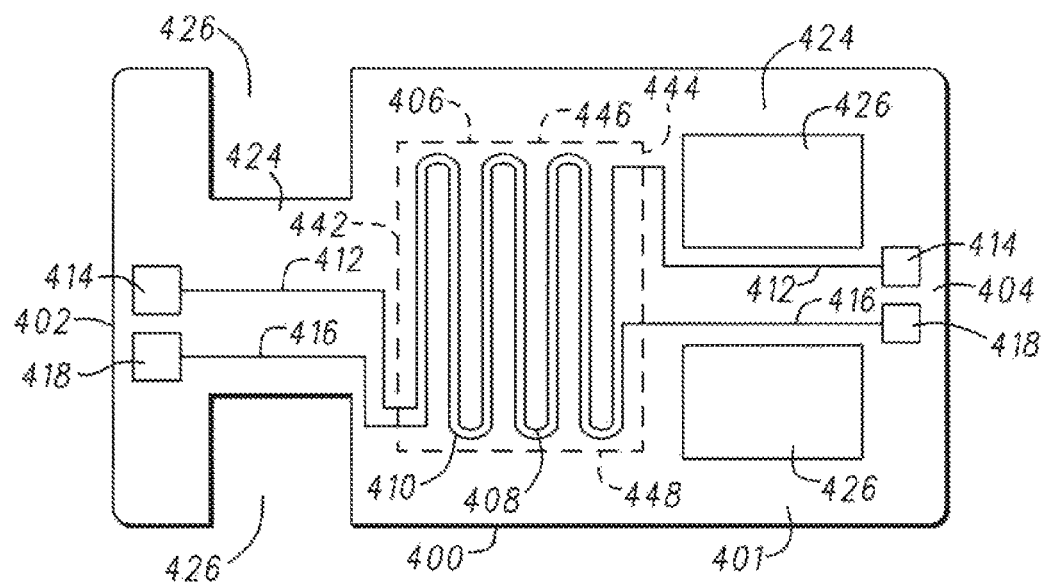
FIG. 4 is a schematic diagram of another example of a stage heater.

FIG. 4 shows a schematic of another example of a stage heater 400. In at least some regards, the stage heater 400 includes similar features to the stage heater 120 previously described herein. For instance, the stage heater 400 includes a heater body panel 401 extending between first and second support mounts 402, 404. A stage heating element 408 is positioned within a stage plane 406 of the stage heater 400 to provide distributed heating over at least a portion of the stage plane 406. In one example, the stage heating element 408 extends between a first stage plane edge 442 a second stage plane edge 444 and between first and second stage plane ends 446 and 448. As further shown in FIG. 4, a temperature sensing element 410 extends in a serpentine configuration corresponding to the serpentine configuration of the stage heating element 408 extending over the stage plane 306. In another example, each of the stage heating element 408 and the temperature sensing element 410 include corresponding heating and sensing leads 412 and 416 and corresponding heating contacts 414 and sensing contacts 418 configured to provide electrical connections for each of the stage heating element and the temperature sensing element 408, 410.

Additionally, in the schematic view shown in FIG. 4, each of the first and second support mounts 402, 404 are coupled by way of one or more bridges 424 extending between the stage plane 406 and the first and second support mounts. For instance, on the left side of the stage heater 400 a single bridge 424 extends between the stage plane 406 and the first support mount 402. In contrast, on the right side of the stage heater 400 the second support mount 404 is spaced from the stage plane 306 by a plurality of bridges 424. In the example shown, three bridges extend between the stage plane 406 and the second support mount 404. In another example one or more bridges such as one or two bridges extend between the stage plane 406 and the second support mount 404. That is to say, with the schematic configuration shown in FIG. 4 the stage heater 400 optionally includes any number of bridges 424 (e.g., one or more) extending between each of the support mounts 402, 404 and the stage plane 406 to provide robust support for the stage plane 406. Accordingly, mechanical engagement of a probe, such as the displaceable probe 116 shown in FIGS. 1 and 2, at any location of the stage plane 406 results in negligible tilting or twisting of the stage plane 406. Providing one or more bridges at each of the interfaces between the first and second support mounts 402, 404 and the stage plane 406 provides mechanical support to the stage plane 406 and thereby accordingly prevents tilting or twisting of the stage plane 406 during mechanical testing. Optionally, the bridges 424 are formed in any one of the different configurations including, but not limited to, linear shapes, curved shapes, non-linear shapes (trapezoidal, switch-backed and the like) to provide robust mechanical support to the stage plane 406 and the sample thereon while at the same time throttling heat transfer from the stage plane 406 to the first and second support mounts 402, 404.

In one example, the stage heater 400 provides at least three point contact between the stage plane 406 and the first and second support mounts 402, 404 through the bridges 424 to substantially prevent tilting of the stage plane 406, for instance during mechanical loading by way of engagement of the displaceable probe with a sample on the stage plane 406. Accordingly, the stage plane 406 is held substantially static while the probe 116 is engaged at any location within the stage plane 406 because of the robust mechanical support provided by the three or more points of contact between the stage plane 406 and the first and second support mounts 402, 404.

In other examples the provision of one or more bridges 424 forms one or more voids 426 to either side of the bridges 424. For instance, as shown on the left side in FIG. 4 voids 426 are provided to either side of the single bridge 424 extending between the first support mount 402 and the stage plane 406. In a similar manner, the provision of two or more bridges 424 on the right side of the stage heater 400 accordingly provides one or more voids such as the two voids 426 shown in FIG. 4 between the two or more bridges 424. In still another example, each of the stage heaters 120 and 400 shown herein include at least first and second support mounts 302, 304. The provision of first and second support mounts 302, 304 and 402, 404 is not intended to be limiting. For instance either of the stage heaters 120, 400 could include a plurality of support mounts, for instance three or more support mounts positioned around the stage plane 306, 406 of each of the stage heaters to thereby provide supplemental support for the stage planes. Further, in another example, the stage planes 306, 406 are optionally supported with a single support mount, such as a ring or semi-circular support mount positioned around at least a portion of the stage planes.

The stage heaters 120, 400 described herein are constructed with materials and in configurations that facilitate the rapid heating of the stage plane of each of the heaters while at the same time throttling heat transfer to each of the first and second support mounts 302, 304. Additionally, the stage heaters are constructed with materials and in configurations to robustly support the stage plane 306 during mechanical testing. Accordingly, the materials of the stage heater 120 (or 400) are thereby selected to provide a rigid supporting stage that also retards heat transfer away from the heated stage plane. Stated another way, a combination of characteristics are desirable for the stage heater 120 including low thermal conductivity, low coefficient of thermal expansion to substantially minimize thermal expansion as well as thermal mechanical drift and a high elastic modulus to provide rigid support to a sample positioned on the stage plane 306.

In one example, the stage heater 120 is constructed with the substrate having a low thermal conductivity such as a thermal conductivity less than or equal to 10 Watts/meter Kelvin. Additionally, for thermal mechanical stability the material should have a low coefficient of thermal expansion, for instance a coefficient of thermal expansion less than or equal to 20 microns per meter or lower. With this combination of mechanical and thermal mechanical properties provided by the materials of the stage heater 120 the stage heater is configured to rapidly heat the stage plane 306 while at the same time cooperating with the bridges 324 and voids 326 (for instance in a vacuum environment) from transmitting heat to the first and second support mounts 302, 304. Heat transfer to other portions of a stage having a larger thermal mass, for instance a stage adaptor or the stage 102, is thereby substantially prevented by this combination of the materials and the geometry of the stage heater 120 between the stage plane 306 and the first and second support mounts 302, 304.

Additionally and as described above, a high elastic modulus is desired for the stage heater 120 to provide robust support for the stage plane 306. In one example, the stage heater 120 (e.g., the substrate of the stage, such as the heater body panel 300), is constructed with a material having an elastic modulus of greater than or equal to 50 GPa. The stage heater 120, including the heater body panel 300, is constructed with, but not limited to, fused quarts, sapphire, zirconium and the like. These materials have thermal conductivities, coefficients of thermal expansion and elastic moduli that localize heating to the stage plane 306 while at the same time cooperating with the bridges 324 and the voids 326 to substantially throttle heat transfer to the first and second support mounts 302, 304 and the stage 102 or other instrument coupled to these features. Additionally, the high elastic modulus provided by these materials provides a rigid support structure for the stage heater 120 that supports a sample positioned on the stage plane 306 in cooperation with the configuration of the support mounts 302, 304 and the bridges 324 (e.g., at least three point support). Mechanical testing of a sample positioned on the stage heater 120 accordingly is performed with consistent and reliable heating and with support of a distributed sampled engaged with the stage plane 306 irrespective of the testing location (or distributed locations) on the sample.

Additionally, the elements used for heating and sensing of temperatures of the stage plane 306 desirably have a high melting point that allows for consistent heating to a desired testing temperature, for instance temperatures greater than 400 degrees Celsius in one example and greater than 1100 degrees Celsius in another example. Optionally, the stage plane 306 of the stage heater 120 is configured to heat a sample to temperatures of 400, 500, 750, 1100 or 1500 degrees Celsius or more. In one example, the stage heating element and the temperature sensing element 308, 310 are constructed with, but not limited to, materials having a high melting point such as a melting point greater than 1500 degrees Celsius. In one example, the stage heating element 308 and the temperature sensing element 310 are constructed with materials including tungsten having a melting point of approximately 3400 degrees Celsius. By providing a heating and sensing element 308, 310 having a high melting point (e.g., a melting point above the operational heating ceiling of the stage heater 120) reliable heating of the stage heater 120 over the lifetime of operation the stage heater is accordingly achieved.

In some examples, the heating and sensing elements 308, 310 are covered with a passivation coating including for instance yttrium oxide, silicon oxide, silicon carbide, silicon nitride or the like. The passivation coating over the heating and sensing elements substantially prevents or retards the development of oxides along the surface of the heating and sensing elements and accordingly ensures that the heating and sensing elements 308, 310 operate consistently over the operational lifetime of the stage heater 120. For instance the heating element 308 rises to a desired temperature with a specified amount of heating power from the controller 106, and the sensing element accurately measures that temperature.

In another example, the stage heaters described herein are constructed with one or more methods of manufacture. In one example, the stage heater 120 is constructed with a microelectromechanical systems manufacturing method (MEMS) including, for instance, steps of deposition, patterning and lithography. In another example, the fabrication method includes focused ion beam lithography, laser cutting and the like. In still other examples, the stage heater 120 is constructed with manufacturing techniques, such as manual component assembly including adhering or lamination of components, such as a substrate layer of the stage heater 120 (e.g., the panel 300) with the stage heating element 308 and the temperature sensing element 310 to form a laminated stage heater 120. In another example, the heater body panel 300 is machined with a micromachining element to provide a channel therein for deposition of a stage heating element or a temperature sensing element 308, 310. Optionally, the temperature sensing element 310 and state heating element 308 are positioned within channels of the heater body panel 300, for instance by manual manufacturing means such as by operation of manipulating and insertion mechanisms that place the elements within channels.

Figure 5:
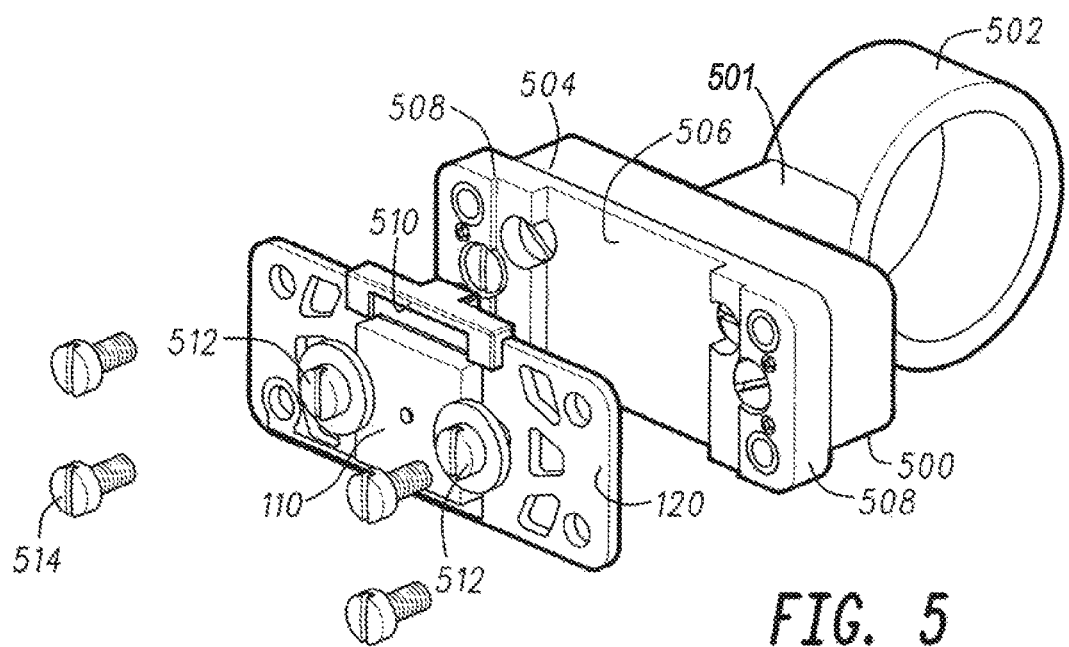
FIG. 5 is a perspective view of a stage heater assembly including one example of a stage adaptor and a stage heater.

FIG. 5 shows one example of a stage adaptor 500 including an adaptor body 501. The stage adaptor 500 is optionally configured for use with the stage 102 shown in FIGS. 1 and 2. The stage adaptor 500 includes a stage assembly coupling feature 502 sized and shaped for engagement with a stage of the testing assembly 100. In one example, the stage assembly coupling feature 502 includes a spindle ring sized and shaped for coupling with a tilt stage spindle assembly of a tilting stage. In another example, the stage adaptor 500 is configured for use with a static, translational or rotational stage, as described herein. In still another example, the stage adaptor 500 is configured for use with another instrument, for instance an objective stage of an optical microscope, transmission or scanning electron microscope, another instrument that would benefit from heating of a sample during testing and the like.

The stage adaptor 500 also includes a stage heater coupling feature 504 sized and shaped to couple with one or more of the stage heaters 120, 400 described herein. As shown in the example, the stage heater coupling feature 504 includes an adaptor recess 506 that is positioned between adaptor legs 508. The stage heater 120 is configured for coupling with the adaptor legs 508 for instance by coupling with the first and second support mounts 302, 304 shown in FIGS. 3A, B. Coupling of the stage heater 120 between the adaptor legs 508 allows for the stage plane 306 to be suspended above the remainder of the stage adaptor 500 by way of the adaptor recess 506. Suspension of the stage plane 306 isolates the stage plane 306 (the actively heated portion of the stage heater 120) from the remainder of the stage adaptor 500. Accordingly, heat transfer from the stage plane 306 is throttled through the one or more bridges 324 shown in FIGS. 3A and 3B without any direct conduction into the stage adaptor 500. Accordingly, the adaptor legs 508 and the adaptor recess 506 cooperate to ensure heating of the stage heater 120 is localized to the stage plane 306 without any substantial heat transfer to the stage adaptor 500 or any other portions of the stage 102 having a large thermal mass.

Referring again to FIG. 5, the sample 110 is shown coupled along the stage heater 120. In one example, the sample 110 is coupled along the stage heater for instance the stage plane 306 with a clip 510 and sample fasteners 512. These optional features are used to provide a clamping engagement to the sample 110 with the stage heater 120 and to engage the sample 110 along the stage plane 306. The surface to surface contact of the sample 110 with the stage plane 306 facilitates conductive heat transfer between the sample 110 and the stage plane 306 coupled with the distributed heating element 308 underlying the stage plane 306. As previously described, the stage heating element 308 covers a substantial portion of the stage plane 306. For instance, the heating element 308 is distributed across the stage plane 306, heats the entire plane, and accordingly conduction through the surface to surface contact between the stage plane 306 and the sample 110 is able to heat substantially the entirety of the sample 110.

Although in the example shown, a clip 510 and sample fasteners 512 are provided to clamp the sample 110 to the stage heater 120 other means of fastening the sample 110 to the stage heater 120 are also available. These methods include, but are not limited to, adhesives, welds, mechanical fittings, interference fits, tongue and groove configurations and the like.

Further, as described previously, a sample having another configuration (e.g., non-planar, irregular, linear, non-linear or the like) is coupled and retained along the stage plane 306 with any one of the means of fastening described herein including, but not limited to, adhesives, fasteners, clamps, welds and the like. Accordingly the stage heater 120 described herein is similarly configured to heat samples having a non-planar configuration. The distributed heating provided by the stage heating element 308 across the stage plane 306 ensures that a sample, including a non-planar sample with two or more points of contact with the stage plane 306, is heated to the same temperature at every point of contact of the sample with the stage plane.

As also shown in FIG. 5, one or more optional heater fasteners 514 are provided for coupling of the stage heater 120 to the stage adaptor 500. In one example, the heater fasteners 514 cooperate with the stage heater 120 and the stage adaptor 500 to anchor the first and second support mounts 302, 304. The anchored first and second support mounts cooperate with the material of the stage heater 120 to provide a robust supported substrate for the sample 110. That is to say, the anchoring of each of the first and second support mounts 302, 304 at the opposed ends of the stage adaptor 500 (e.g., on the adaptor legs 508) minimizes the deflection of the stage heater 120 upon engagement with a displaceable probe for instance a displaceable probe engaged with the sample 110 (e.g., in compression, tension, lateral scratching movement and the like). In addition, the robust mechanical properties of the stage heater 120 (for instance by way of the materials selected and the three or more points of support of the stage plane 306) cooperate with the anchoring features of the first and second support mounts 302, 304 to provide a rigid substrate that supports the sample 110 while at the same time heating the sample as described herein.

Figure 6:
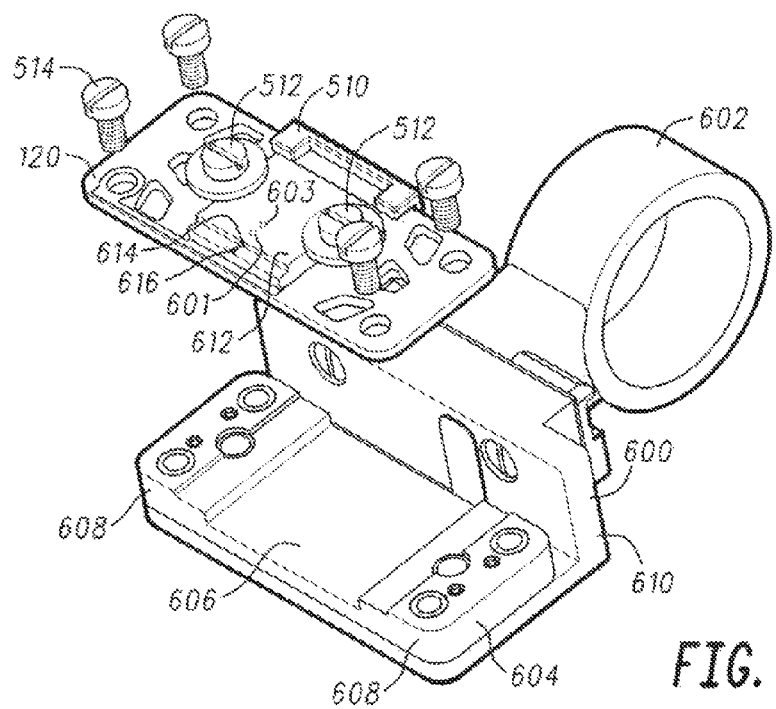
FIG. 6 is a perspective of view of a stage heater assembly including another example of a stage adaptor and a stage heater.

FIG. 6 shows another example of a stage adaptor 600 configured for tensile testing of a sample such as the tensile sample 612 shown in the figure. In the example shown, the tensile sample 612 includes at least one sample shaft 614 and a sample head 616 at one end of the sample shaft 614. Optionally, a plurality of sample shafts 614 and sample heads 616 having differing dimensions, materials and the like are formed along the sample 612. The adaptor 600 orients the stage heater 120 as well as the tensile sample 612 orthogonally to the orientation shown in FIG. 5. The probe 116 including the probe heater 122 further described herein is provided with a tensile gripping tip sized and shaped to engage around the sample head 616 and thereby apply a tension force to the sample shaft 614. The stage adaptor 600 and the sample 612 are also usable in other configurations including, but not limited to, compression testing. One or more sample shafts are provided along the sample and are tested with a planar punch tip or other instrument that loads the shafts in compression.

Referring to FIG. 6 again, the stage adaptor 600 is shown with a stage assembly coupling feature 602. In one example, the stage assembly coupling feature includes a spindle ring sized and shaped for coupling with a tilting stage of the stage 102 shown in FIGS. 1 and 2. In another example, the stage assembly coupling feature 602 is sized and shaped for coupling with stages for use with one or more instruments including, but not limited to, static stages, translational stages, rotational stages and the like used for instance as objective stages with optical and electron based microscopes and other instruments that benefit from heating of a sample. As further shown in FIG. 6, the stage adaptor 600 includes a stage coupling feature 604 sized and shaped to receive the stage here 120 thereon for coupling to opposed adaptor legs 608. As with the stage adaptor 500 the stage adaptor 600 further includes an adaptor recess 606 sized and shaped to isolate the stage plane 306 and thereby ensure localized heating of the tensile sample 612 with minimal heat transfer to the remainder of the stage adaptor 600 and any component coupled with the stage adaptor such as the stage 102.

As further shown in FIG. 6, the stage adaptor 600 includes an elbow 610 that positions the stage heater 120 in the orthogonal orientation relative to the orientation shown in FIG. 5. That is to say, the elbow 610 provides an angled feature having the stage heater coupling feature 604 thereon. The stage heater 120 is thereafter coupled to the adaptor legs 608 in the orthogonal orientation to provide the tensile sample 612 including the sample shaft 614 and the sample head 616 in the orientation shown in FIG. 6 for tensile testing by the displaceable probe 116 coupled with the transducer assembly 104. Optionally, the elbow 610 orients the stage heater 120 as well as a sample thereon in any number of orientations according to the configuration of the elbow.

The stage adaptors 500, 600 shown herein are constructed with a rigid material configured to provide support to the stage heater 120 during a mechanical testing procedure. The forces applied to the sample are transmitted in at least some degree to the stage adaptors 500, 600. The stage adaptors 500, 600 cooperate with the remainder of the stage 102 to provide a rigid support structure to the sample and thereby accordingly minimal deflection or displacement of the sample 612, 110 during the mechanical testing scheme. In one example, the stage adaptors are constructed with a rigid material (e.g., having a relatively high elastic modulus of at least 50 GPa) including, but not limited to, alumina, stainless steel, titanium and the like.

Figure 7:
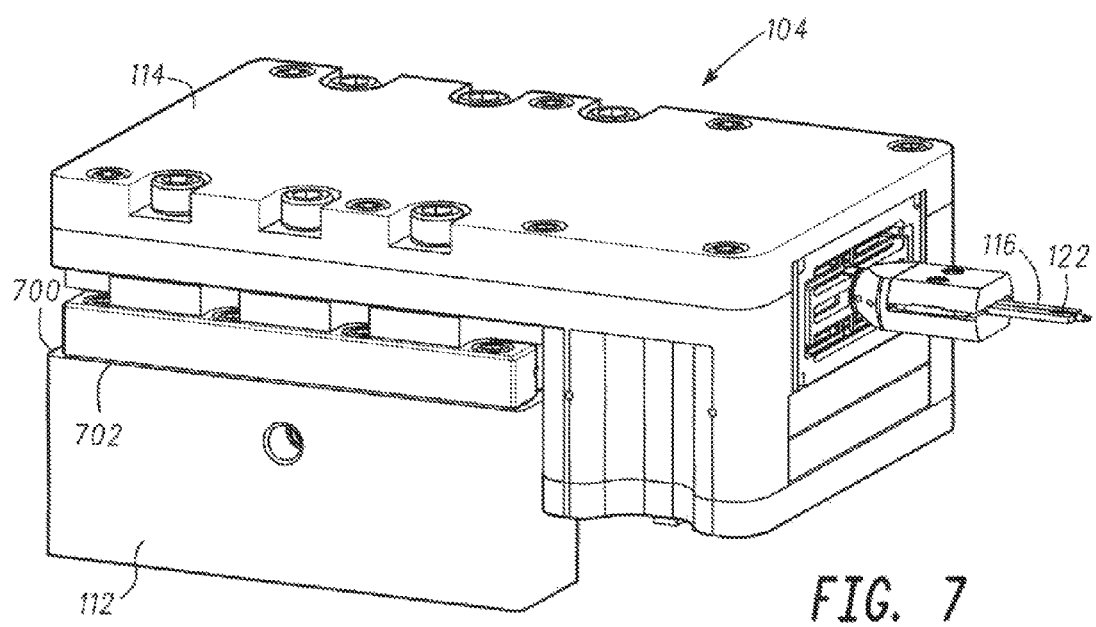
FIG. 7 is a perspective view of one example of a transducer assembly.
Figure 8:
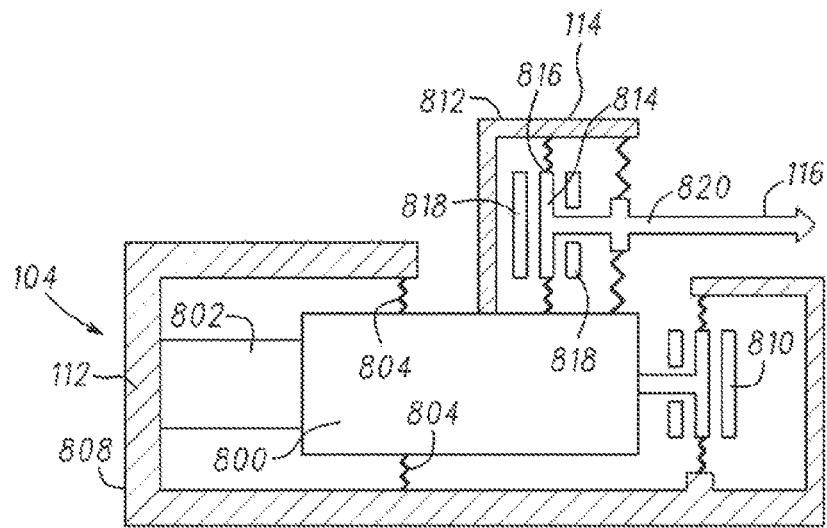
FIG. 8 is a schematic view of the transducer assembly of FIG. 7 including a flexural actuator and a transducer.

Referring now to FIGS. 7 and 8, one example of the transducer assembly 104 is shown in detail. Referring first to FIG. 7, the transducer assembly 104 is shown including the flexural actuator 112 and the transducer 114 coupled with the flexural actuator 112. In one example, the transducer assembly 104 has a modular construction. For instance, the flexural actuator 112 includes a transducer interface profile 700 and the transducer 114 includes an actuator interface profile 702. The transducer interface profile 700 is sized and shaped to mate with a plurality of actuator interface profiles 702 provided with a family of transducers having a corresponding configuration. That is to say, the transducer 114 coupled with the flexural actuator 112 may be one transducer in a family of transducers. The transducer 114 may be changed out for any number of load cells having a variety of displacement and force ranges. Additionally, each of the transducers 114 coupled with the flexural actuator 112 may provide one or more additional testing mechanisms including for instance tensile, compression, scratch testing, three dimensional movement of the displaceable probe 116 and the like. As further shown in FIG. 7, the displaceable probe 116 is coupled with the transducer 114, and the probe 116 includes the probe heater 122 previously described and shown in FIG. 1.

Referring now to FIG. 8, a schematic representation of the transducer assembly 104 is provided. As shown, the transducer assembly 104 includes the flexural actuator 112 and the transducer 114 as previously described herein. Referring first to the flexural actuator 112, the flexural actuator includes a flexure mechanism 800 suspended by spring supports 804 within the actuator housing 808. An actuator motor 802 is coupled with the flexure mechanism 800 to provide translational movement to the flexure mechanism 800. The flexure mechanism 800 ensures that movement of the actuator motor 802 is provided to the transducer 114 in a linear fashion. That is to say, the flexure mechanism 800 converts the motion provided by the actuator motor 802 through a series of linkages within the flexure mechanism 800 to ensure the corresponding movement transmitted to the transducer 114 is purely linear, for instance along the access of the displaceable probe 116.

In another example, the flexural actuator 112 further includes a sensor 810 such as a displacement sensor coupled with the flexure mechanism 800. In one example the displacement sensor 810 includes but is not limited to a capacitive sensor having two or more plates. In the example shown a center plate is suspended between two static opposed plates. Movement of the center plate relative to the opposed plates is detected by the sensor 810, for instance by a change in capacitance that is measured by the testing assembly 100 for instance the transducer control module 126 previously shown in FIG. 1.

In the example shown in FIG. 8, the transducer 114 includes a transducer housing 812 coupled with the flexure mechanism 800 and a capacitive transducer 814 suspended within the transducer housing 812. In the example shown the capacitive transducer 814 includes a deflectable center plate 816 bracketed by opposed static plates 818. The opposed plates 818 are static relative to the transducer housing 812. Corresponding movement of the center plate 816 is thereby measurable by the capacitive transducer 814, and in at least one example may be measured by the transducer control module 126 shown in FIG. 1 to determine the displacement of the probe 116 for instance during a testing procedure where the probe 116 is engaged with the sample on the stage surface 118 including for instance the stage heater 120 shown in FIG. 1. As shown in FIG. 8, a coupling shaft 820 couples the displaceable probe 116 with the center plate 816. Accordingly, movement of the displaceable probe 116 is transmitted along the coupling shaft 820 and accordingly results in movement of the center plate 816 which is measurable by the capacitive transducer 814 to determine the displacement of the displaceable probe 116.

In one example, the transducer assembly 104 is operated with the flexural actuator 112 to provide the translation of the displaceable probe 116. That is to say, the operation of the actuator motor 802 is transmitted through the flexure mechanism 800 to the transducer 114 to accordingly move the displaceable probe 116 (for instance, a heated displaceable probe) into engagement with a sample and for performance of a testing scheme on the sample including, but not limited to, indentation, scratching, tensile, compression testing and the like. In the example where the flexural actuator 112 provides the translation of the displaceable probe 116 the capacitive transducer 814 of the transducer 114 is in one example used to measure the movement of the displaceable probe 116 relative to the transducer housing 812 (e.g., movement of the center plate 816 relative to the opposed plates 818). In still another example, the flexural actuator 112 is used as a gross positioning element to move the displaceable probe 116 into close proximity to a sample, for instance a sample positioned on the stage 102. The transducer 114 is thereafter operated to move the displaceable probe 116 to engage the probe 116, conduct a testing procedure, and at the same time measure the displacement of the displaceable probe 116 during the procedure.

Figure 9:
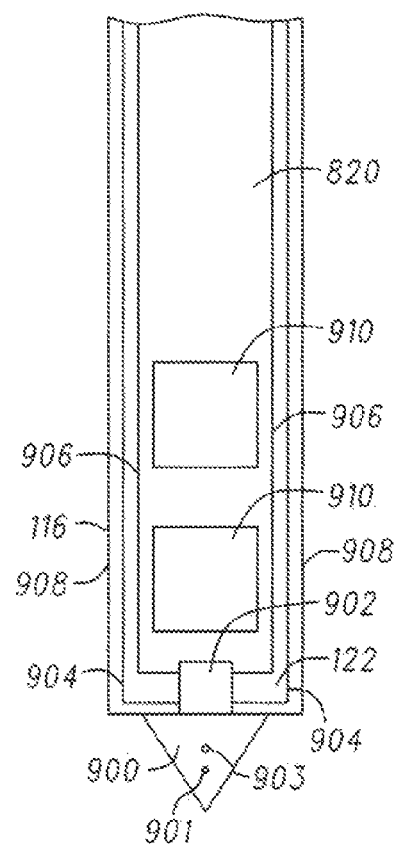
FIG. 9 is a schematic view of one example of a probe heater coupled with a probe for use with the transducer assembly of FIGS. 7 and 8.

FIG. 9 shows a schematic example of the displaceable probe 116. The displaceable probe 116 includes a coupling shaft 820 extending to a probe tip 900. As shown in FIGS. 1 and 2, in one example the displaceable probe 116 includes a probe based heater 122 for positioned adjacent to the probe tip 900. The probe heater 122 is configured to heat the probe tip 900 while heat transfer to the remainder of the displaceable probe such as the coupling shaft 820 is substantially throttled by one or more features of the probe heater 122.

As shown in FIG. 9, the probe heater 122 includes heating and sensing elements 902 positioned adjacent to the probe tip 900. As further shown in the figure heating leads 904 and sensing leads 906 extend proximally from the probe tip 900 along the coupling shaft 820 for electrical connection with corresponding features within the transducer 114 shown in FIGS. 1 and 2. Positioning of the heating and sensing elements 902 adjacent to the probe tip 900 ensures that the heating element 902 is able to rapid heat the proximate probe tip 900. Additionally, in one example the displaceable probe 116 includes one or more support columns 908 and voids 910 configured to substantially throttle heat transfer away from the probe tip 900 and the heating and sensing elements 902 along the coupling shaft 820.

In one example, two or more support columns 908 are positioned on either side of the displaceable probe 116. The support columns 908 have a smaller cross-sectional area relative to the overall cross-sectional area of the coupling shaft 820. The smaller cross-sectional area in the direction of heat transfer from the heating and sensing elements 902 toward the proximal portions of the displaceable probe 116 throttles heat transfer into the remainder of the probe 116 and accordingly localizes heating of the probe heater 122 to the probe tip 900 and that portion of the coupling shaft 820 adjacent to the probe tip 900. Additionally, with the provision of one or more support columns 908 one or more voids 910 are provided to the sides of the support columns 908. In a vacuum environment, the voids 910 substantially prevent the heat transfer to the proximal portions of the probe 116. Accordingly, heat generated adjacent to the probe tip 900 by the probe heater 122 is substantially localized to that area of the coupling shaft adjacent to the probe tip 900.

In one example, the displaceable probe is constructed with a material such as quartz. As previously described herein, quartz has a low coefficient of thermal expansion and thermal conductivity while at the same time providing a relatively high elastic modulus. The coupling shaft 820 in combination with the probe tip 900 thereby provides a rigid probe assembly configured to engage the sample coupled with the stage 102 as shown in FIGS. 1 and 2. The rigid nature of the displaceable probe 116 allows for accurate and reliable mechanical testing of the sample on the stage 102. Additionally the material selection as well as the cooperation of the material selection with the support columns 908 and the voids 910 substantially throttles heat transfer proximally from the heating and sensing elements 902 into the remainder of the coupling shaft 820 and the transducer 114 having larger thermal masses.

Additionally, as with the stage heater 120 previously described herein the heating and sensing elements 902 including the heating and sensing leads 904, 906 are in one example constructed with a material having a high melting point, for instance a melting point greater than 1500 degrees Celsius. The heating leads and sensing leads and the heating and sensing elements 904, 906, 902 are constructed with, but not limited to, a material such as tungsten having a melting point of approximately 3400 degrees Celsius or another material having a melting point greater than the desired temperature ceiling of the probe heater 122. By using a material having a high melting point the probe heater 122 is able to heat the probe tip 900 to a desired temperature for instance greater than 400 degrees Celsius. In another example, the probe heater 122 is able to heat the probe tip 900 to temperatures of 500, 750, 1100 or 1500 degrees Celsius.

Optionally, a passivation layer such as silicon oxide, silicon carbide, silicon nitride, yttrium oxide or the like is applied to the heating and sensing elements 902 as well as the heating and sensing leads 904, 906 to substantially prevent or retard oxidation of the elements and leads. Accordingly, the heating and sensing elements 902 as well their respective leads are able to operate over the lifetime of the displaceable probe 116 in a reliable and consistent manner without any substantial attenuation in performance.

Additionally, the heating system 108 described herein, including for instance one or more of the probe tip 900 and the stage surface 118 (e.g., the stage plane 306) is also configured for use with any mechanical, electro-mechanical or electrical based testing assembly or instrument that would benefit from one or more of a heated sample or probe. For instance, for electrical, electro-mechanical, thermo-electrical, or thermo-electro-mechanical testing (e.g., electrical based testing), a voltage or current is applied through the probe and the sample and the resistance or capacitance change of the sample or probe-sample contact area is measured, for instance with an electrical characteristic module of the controller 106 (e.g., within the memory system 132). In another example, electrical, electro-mechanical, thermo-electrical, or thermo-electro-mechanical testing is conducted with the sample electrically connected (e.g., by way of voltage or current application) to measure the resistance or capacitance change while the sample is heated, mechanically stressed or both. With this measurement scheme only the sample is connected to the source of electricity and only the sample is measured. The probe 116 may optionally provide mechanical pressure (or force) to the sample but is not used to measure the electrical properties of the sample. In another example, the probe 116 also conducts mechanical testing during the electrical based testing.

As described herein and shown in FIGS. 6 and 9 the electrical connections, such as contacts for providing electricity to one or more of the probe tip 900, the stage surface 118 (stage plane 306) or the sample directly, are shown in FIGS. 6 and 9. For instance, as shown in FIG. 6, a voltage application contact 601 and a current application contact 603 are provided adjacent to the sample shaft 614. In this configuration, the stage plane 306 or the portion of the stage plane 306 associated with the contacts 601, 603 is electrically isolated from the remainder of the stage surface (e.g., the remainder of the stage heater 120). Similarly, the probe tip 900 includes a corresponding voltage application contact 901 and a current application contact 903. Leads extend proximally along the coupling shaft 820 and optionally through the stage 102 to power the contacts. The contacts 601, 603, 901, 903 are used for the testing methods described herein including, but not limited to, 2 point probe measurement, 4-point probe measurement and the like. Optionally, the voltage application contact 601 and the current application contact 603 are coupled directly with the sample, and leads are run directly from the sample to apply one or more of voltage or current for electrical testing.

With the probe tip 900, the portion that contacts a sample may be electrically conductive (e.g. tungsten, conductive diamond, etc.). With electrical insulation between the probe tip 900 and the remainder of the probe (e.g., the probe heater 122, the coupling shaft 820 and the like), at least a portion of the tip 900 is electrically isolated from the rest of the probe. Additional leads are attached to one or more of the voltage application contact 901 or the current application contact 903 to accordingly electrically test through the probe tip 900. Optionally, as described above, the sample is electrically isolated from the probe tip 900 and the stage heater 120 (e.g., the stage surface 118), and electrical leads are coupled directly with the sample for electrical based testing of the sample. The system (e.g., the system 100) is accordingly used for electrical measurements in conjunction with (or separately from) heating and mechanical testing. For example, the contacts on the probe 901, 903 along with the contacts attached to the sample (e.g., 601, 603) are part of a 4-point electrical measurement system that monitors and measures electrical resistivity changes during tensile or compressive deformation of the sample. In another example, additional leads and contacts are provided to the sample (110 or 612), the stage surface 118 (e.g., the stage plane 306 isolated from the remainder of the stage heater 120) for more extensive electrical measurements.

Figure 10:
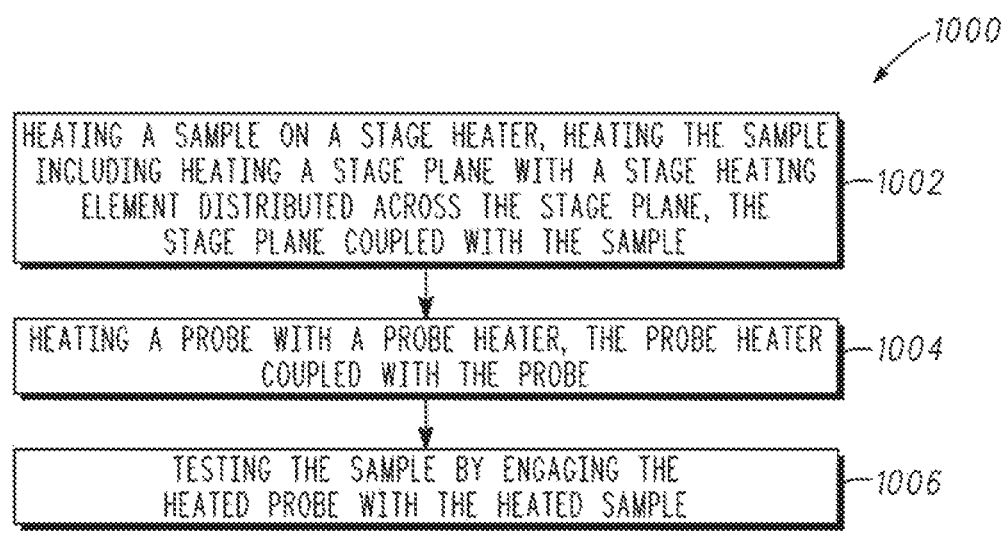
FIG. 10 is a block diagram showing one example of a method of mechanically testing a sample with a testing assembly including a stage heater and a probe heater.

FIG. 10 shows one example of a method 1000 for mechanically testing a sample with a testing assembly such as the assembly 100 at a scale of microns or less. In describing the method 1000 reference is made to one or more components, features, functions, and the like previously described herein. Where convenient reference is made to the components and features with reference numerals. The reference numerals provided are exemplary and are not exclusive. For instance, the features, components, functions and the like described in the method 1000 include the corresponding numbered elements, other corresponding features described herein (both numbered and unnumbered) as well as their equivalents.

At 1002, the method 1000 includes heating a sample such as the sample 110 on a stage heater 120. Heating the sample includes heating a stage plane 306 with a stage heating element 308 distributed across the stage plane, for instance across a back side of the stage plane opposed to the surface of the stage heater 120 configured for reception of the sample thereon. Optionally, heating the sample 110 includes heating the stage plane 306 with the stage heating element 308 extending from a first stage plane edge 332 to a second stage plane edge 334 and between a first stage plane end 336 and a second stage plane end 338. Additionally, in another example heating the sample 110 includes distributing heat over the entire stage plane 306 according to the stage heating element distributed across the stage plane 306. That is to say, with the stage heating element 308 having the width of the individual passes of the element as well as the distribution of the element across the stage plane 306, for instance in a serpentine pattern, the stage heating element 308 is configured to reliably and consistently heat the entirety of the stage plane 306 to a desired temperature without any substantial gradient of temperature across the stage plane 306. Accordingly, a sample as described herein (e.g., a sample with a distributed planar configuration) coupled along the stage plane 306 is consistently heated to a single temperature without any corresponding temperature gradient in the sample.

In one example, the sample is coupled with the stage plane 306 with one or more fastening mechanisms, for instance fasteners that provide surface to surface engagement between the sample 110 and the stage plane 306. Methods of fastening the sample to the stage plane 306 include, but are not limited to, clamping, fastening, adhering, welding, mechanically interfitting and fusing the sample to the stage heater 120.

In another example, heating the sample 110 includes heating the stage plane 306 to a temperature greater than 400 degrees Celsius. In still another example, heating the sample includes heating the stage plane 306 to a temperature greater than 1100 degrees Celsius. In yet another example, heating the sample includes heating the stage plane 306 to a temperature greater than 1100 degrees Celsius while the two or more support mounts 302, 304 of the stage heater 120 are passively heated to a temperature of 150 degrees Celsius or less. That is to say, with the one or more bridges 324 and the voids 326 (for instance in a vacuumed environment) as well as the material selection of the stage heater 120 heat transfer from the stage plane 306 is throttled to the first and second support mounts 302, 304 to ensure the first and second support mounts have a temperature that is negligibly raised relative to the elevated temperature of the stage plane 306. The relatively low temperatures of the first and second support mounts 302, 304 substantially retard the transmission of heat to the remainder of a stage coupled with the stage heater 120 for instance the stage 102 shown in FIGS. 1 and 2. Accordingly, undesirable characteristics such as thermal mechanical drift, thermal expansion and the like are substantially prevented with larger components having greater thermal masses relative to the stage heater 120. Optionally throttling heat transfer from the stage plane 306 to the two or more support mounts includes throttling heat transfer through at least a first bridge extending between the stage plane 306 and one of the two or more support mounts such as the first and second support mounts 302, 304. Additionally, throttling heat transfer from the stage plane 306 to the two or more support mounts includes throttling heat transfer through a second bridge 324 extending between the stage plane 306 and another of the two or more support valves for instance the second support mount 304.

At 1004, the method 1000 includes heating a probe such as the displaceable probe 116 shown in FIGS. 1 and 2 with a probe heater 122. The probe heater 122 is coupled with the probe 116. For instance, as shown in FIG. 9 the probe heater 122 is coupled in close proximity to the probe tip 900 to localize heating of the probe tip 900 and thereby substantially ensure the heating of the probe tip 900 without significant heating of the remainder of the probe 116. In at least one example the displaceable probe 116 including the probe heater 122 includes one or more support columns 908, voids 910 and material selection configured to substantially throttle heat transfer from the heating and sensing elements 902 proximally along the coupling shaft 820.

In yet another example, the method 1000 includes controlling heating of the sample 110 and the probe 116 such as the probe tip 900 to substantially the same temperature before mechanical testing (engagement of a probe tip with the sample 110). By heating both of the probe 116 and the sample 110 to substantially the same temperature, for instance with the heater control module 128 shown in FIG. 1, the probe 116 is elevated to a temperature matching that of the sample 110 prior to engagement of the probe 116 with the sample. The matching of temperatures substantially precludes heat transfer from the sample 110 to an otherwise unheated displaceable probe 116. Accordingly, the sample 110 is maintained at the desired temperature during the mechanical testing procedure to ensure that the mechanical characteristics measured by the transducer assembly 104 are accurately determined at the appropriate desired temperature for the sample 110.

At 1006, the sample 110 is mechanically testing by engaging the heated probe 116 with the heated sample 110. Optionally, mechanical testing includes one or more of deformation based tests of the heated sample 110 with the heated probe 116. The deformation based tests include, but are not limited to, compression testing, tensile testing, indentation testing, scratch testing, tribology testing and the like. Mechanical testing accordingly includes one or more probes 116 configured to conduct the testing procedures including indentation and scratching probes, planar punch probes for compression testing, tensile gripping probes and the like.

As previously described herein the stage heater 120 provides distributed heating across the stage plane 306 that accordingly heats the sample 110 positioned on the plane. In a similar manner, the probe heater 122 heats the displaceable probe 116 including for instance the probe tip 900 to a substantially matching desired temperature. As the mechanical testing procedure is begun the heated probe tip 116 engages with and mechanically tests the sample 110 while both are at the elevated temperature. In another example, mechanically testing the sample 110 includes mechanically testing the sample at a plurality of locations on the sample for instance a plurality of locations spread over the sample (e.g., where the sample is distributed across the stage plane 306). In one example, the sample 110 has a distributed planar geometry provided across the stage plane 306. By providing a distributed heating element 308 along the stage plane 306 each of the locations for testing of the sample 110 are elevated to the desired temperature and consistently remain at that temperature during mechanical testing.

Various Notes & Examples

Example 1 can include subject matter such as a testing assembly for use in testing at a scale of microns or less, the testing system comprising: a heating system configured to heat a sample and a probe, the heating system including: a stage heater having a stage plane and a stage heating element distributed across the stage plane, the stage heater configured to heat a sample positioned on the stage plane, and a probe heater having a probe heating element coupled with a probe configured for testing the sample coupled with the stage plane, the probe heater configured to heat the probe; a stage coupled with the stage heater; and a transducer assembly coupled with the probe heater.

Example 2 can include, or can optionally be combined with the subject matter of Example 1, to optionally include a testing assembly platform configured for coupling with an instrument, and the stage and the transducer assembly are coupled with the testing assembly platform.

Example 3 can include, or can optionally be combined with the subject matter of one or any combination of Examples 1 or 2 to optionally include wherein the stage is a multiple degree of freedom stage configured to move the stage plane according to the multiple degrees of freedom.

Example 4 can include, or can optionally be combined with the subject matter of one or any combination of Examples 1 through 3 to optionally include wherein the multiple degree of freedom stage includes at least one of rotation or tilt stages, and the stage heater is coupled with one of the rotation or tilt stages.

Example 5 can include, or can optionally be combined with the subject matter of one or any combination of Examples 1-4 to include wherein transducer assembly includes: a flexural actuator having a transducer interface profile, and a transducer having an actuator interface profile, wherein the transducer is removably coupled with the flexural actuator at the transducer and actuator interface profiles.

Example 6 can include, or can optionally be combined with the subject matter of Examples 1-5 to optionally include wherein the stage heater includes a sensing element extending along the stage heating element.

Example 7 can include, or can optionally be combined with the subject matter of Examples 1-6 to optionally include a stage adaptor including: a stage assembly coupling feature configured to couple the stage adaptor with a stage assembly, and a stage heater coupling feature configured to couple the stage heater with the stage adaptor, and the stage heater coupling feature is recessed from the stage plane of the stage heater.

Example 8 can include, or can optionally be combined with the subject matter of Examples 1-7 to optionally include wherein the stage heater coupling feature orients the stage plane orthogonally to the probe in a compression testing configuration.

Example 9 can include, or can optionally be combined with the subject matter of Examples 1-8 to optionally include wherein the stage heater coupling feature orients the stage plane parallel to the probe in a tensile testing configuration.

Example 10 can include, or can optionally be combined with the subject matter of Examples 1-9 to optionally include wherein the stage heating element covers the stage plane from a first stage plane edge to a second stage plane edge and from a first stage plane end to a second stage plane end.

Example 11 can include, or can optionally be combined with the subject matter of Examples 1-10 to optionally include wherein the stage heater includes: two or more support mounts on opposed sides of the stage plane, and a first bridge extending from the stage plane to a first mount of the two or more support mounts, and a second bridge extending from the stage plane to a second mount of the two or more support mounts.

Example 12 can include, or can optionally be combined with the subject matter of Examples 1-11 to optionally include wherein the stage heater includes a heater body panel, and the stage plane, the two or more support mounts and the first and second bridges are included in the heater body panel.

Example 13 can include, or can optionally be combined with the subject matter of Examples 1-12 to optionally include wherein the stage plane is configured to reach temperatures of more than 400 degrees Celsius.

Example 14 can include, or can optionally be combined with the subject matter of Examples 1-13 to optionally include wherein the stage plane is configured to reach temperatures of more than 1100 degrees Celsius.

Example 15 can include, or can optionally be combined with the subject matter of Examples 1-14 to optionally include a controller coupled with the stage heater and the probe heater, and the controller is configured to control heating of the stage heater and the probe heater.

Example 16 can include, or can optionally be combined with the subject matter of Examples 1-15 to optionally include subject matter than can include a heating system for use in testing at a scale of microns or less, the heating system including a stage heater including: a stage plane, a stage heating element distributed across the stage plane, two or more support mounts on opposed sides of the stage plane, and a first bridge extending from the stage plane to a first mount of the two or more support mounts, and a second bridge extending from the stage plane to a second mount of the two or more support mounts.

Example 17 can include, or can optionally be combined with the subject matter of Examples 1-16 to optionally include wherein the stage heater includes a heater body panel, and the stage plane, stage heating element, the two or more support mounts and the first and second bridges are included in the heater body panel.

Example 18 can include, or can optionally be combined with the subject matter of Examples 1-17 to optionally include wherein the stage heating element covers the stage plane from a first stage plane edge to a second stage plane edge and from a first stage plane end to a second stage plane end.

Example 19 can include, or can optionally be combined with the subject matter of Examples 1-18 to optionally include wherein the stage heating element is distributed across the stage plane in a serpentine pattern extending from a first stage plane edge to a second stage plane edge and from a first stage plane end to a second stage plane end.

Example 20 can include, or can optionally be combined with the subject matter of Examples 1-19 to optionally include wherein the stage heater includes a temperature sensing element coextensive with the stage heating element.

Example 21 can include, or can optionally be combined with the subject matter of Examples 1-20 to optionally include wherein the two or more support mounts are laterally spaced from the stage plane by the first and second bridges, the first and second bridges having a cross sectional area in a section orthogonal to a direction of heat transfer toward the two or more support mounts smaller than a cross sectional area of the stage plane or either of the two or more support mounts in the direction of heat transfer.

Example 22 can include, or can optionally be combined with the subject matter of Examples 1-21 to optionally include wherein at least one of the first and second bridges includes a plurality of bridges, and voids are positioned between the bridges of the plurality of bridges, and the plurality of bridges provide three or more points of support to the stage plane from the two or more support mounts.

Example 23 can include, or can optionally be combined with the subject matter of Examples 1-22 to optionally include wherein the stage plane is configured to reach temperatures of more than 400 degrees Celsius.

Example 24 can include, or can optionally be combined with the subject matter of Examples 1-23 to optionally include wherein the stage plane is configured to reach temperatures of more than 1100 degrees Celsius.

Example 25 can include, or can optionally be combined with the subject matter of Examples 1-24 to optionally include wherein the two or more support mounts are configured to reach a temperature of less than 150 degrees Celsius while the stage plane is at a temperature of at least 1100 degrees Celsius.

Example 26 can include, or can optionally be combined with the subject matter of Examples 1-25 to optionally include a stage adaptor, the stage adaptor including: an adaptor body, a stage assembly coupling feature coupled with the adaptor body, the stage assembly coupling feature configured to couple the stage adaptor with a stage assembly, and a stage heater coupling feature coupled with the adaptor body, the stage heater coupling feature configured to couple the stage heater with the stage adaptor.

Example 27 can include, or can optionally be combined with the subject matter of Examples 1-26 to optionally include a sample fixing feature configured to fix a sample over the sample plane.

Example 28 can include, or can optionally be combined with the subject matter of Examples 1-27 to optionally include wherein at least the stage heating element is coated with a passivation layer.

Example 29 can include, or can optionally be combined with the subject matter of Examples 1-28 to optionally include subject matter than can include a method of testing a sample with a testing assembly at a scale of microns or less or instructions for performing the method with the testing assembly including heating a sample on a stage heater, heating the sample including heating a stage plane with a stage heating element distributed across the stage plane, the stage plane coupled with the sample; heating a probe with a probe heater, the probe heater coupled with the probe; and testing the sample by engaging the heated probe with the heated sample.

Example 30 can include, or can optionally be combined with the subject matter of Examples 1-29 to optionally include wherein heating the sample includes heating the stage plane with the stage heating element extending from a first stage plane edge to a second stage plane edge and from first stage plane end to a second stage plane end.

Example 31 can include, or can optionally be combined with the subject matter of Examples 1-30 to optionally include wherein heating the sample includes distributing heat over the entire stage plane according to the stage heating element distributed across the stage plane.

Example 32 can include, or can optionally be combined with the subject matter of Examples 1-31 to optionally include wherein heating the sample includes heating the stage plane to a temperature greater than 400 degrees Celsius.

Example 33 can include, or can optionally be combined with the subject matter of Examples 1-32 to optionally include wherein heating the sample includes heating the stage plane to a temperature greater than 1100 degrees Celsius.

Example 34 can include, or can optionally be combined with the subject matter of Examples 1-33 to optionally include wherein heating the sample includes heating the stage plane to a temperature greater than 1100 degrees Celsius while two or more support mounts are passively heated to a temperature of 150 degrees Celsius or less.

Example 35 can include, or can optionally be combined with the subject matter of Examples 1-34 to optionally include throttling heat transfer from the stage plane to two or more support mounts arranged on opposed sides of the stage plane, the two or more support mounts laterally spaced from the stage plane.

Example 36 can include, or can optionally be combined with the subject matter of Examples 1-35 to optionally include wherein throttling heat transfer from the stage plane to the two or more support mounts includes throttling heat transfer through a first bridge extending between the stage plane and one of the two or more support mounts and throttling heat transfer through a second bridge extending between the stage plane and another of the two or more support mounts.

Example 37 can include, or can optionally be combined with the subject matter of Examples 1-36 to optionally include mounting the stage heater to a stage, the stage heater including a heater body panel, and the stage plane, two or more support mounts and first and second bridges extending between the stage plane and the two or more support mounts are included in the heater body panel.

Example 38 can include, or can optionally be combined with the subject matter of Examples 1-37 to optionally include controlling heating of the sample and the probe to substantially the same temperature before testing.

Example 39 can include, or can optionally be combined with the subject matter of Examples 1-38 to optionally include wherein testing includes one or more of indentation testing or scratch testing of the sample with the heated probe.

Example 40 can include, or can optionally be combined with the subject matter of Examples 1-39 to optionally include wherein testing includes one or more of compression testing or tensile testing of the sample with the heated probe.

Example 41 can include, or can optionally be combined with the subject matter of Examples 1-40 to optionally include wherein testing includes mechanically testing at a plurality of locations on the sample, the plurality of locations spread over the sample plane.

Example 42 can include, or can optionally be combined with the subject matter of Examples 1-41 to optionally include orienting the sample relative to the probe with a stage coupled with the stage heater and the sample.

Example 43 can include, or can optionally be combined with the subject matter of Examples 1-42 to optionally include wherein orienting the sample relative to the probe includes moving the sample in two or more degrees of freedom.

Example 44 can include, or can optionally be combined with the subject matter of Examples 1-43 to optionally include wherein orienting the sample relative to the probe includes moving the sample in one or more degrees of freedom including rotating or tilting of the sample.

Example 45 can include, or can optionally be combined with the subject matter of Examples 1-44 to optionally include wherein testing includes electrically testing the sample with two or more electrical contacts in electrical communication with the sample.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A testing assembly for use in testing at a scale of microns or less, the testing system comprising:
    a heating system configured to heat a sample and a probe, the heating system including:
        a stage heater having a stage plane and a stage heating element distributed across the stage plane, the stage plane including a central planar portion and a perimeter planar portion, and
        wherein the stage heating element and the stage plane each continuously extend from the central planar portion to the perimeter planar portion, the stage heater configured to heat a sample positioned on the stage plane;
    a probe heater having a probe heating element coupled with a probe configured for testing the sample coupled with the stage plane, the probe heater configured to heat the probe;
    a stage coupled with the stage heater; and
    a transducer assembly coupled with the probe.

2. The testing assembly of claim 1 comprising a testing assembly platform configured for coupling with an instrument, and the stage and the transducer assembly are coupled with the testing assembly platform.

3. The testing assembly of claim 1, wherein the stage is a multiple degree of freedom stage configured to move the stage plane according to the multiple degrees of freedom.

4. The testing assembly of claim 1, wherein the stage heater includes a sensing element extending along the stage heating element.

5. The testing assembly of claim 1 comprising a stage adaptor including:
    a stage assembly coupling feature configured to couple the stage adaptor with a stage assembly, and a stage heater coupling feature configured to couple the stage heater with the stage adaptor, and the stage heater coupling feature is recessed from the stage plane of the stage heater.

6. The testing assembly of claim 5, wherein the stage heater coupling feature orients the stage plane in:

an orthogonal orientation to the probe in a compression testing configuration, or a parallel orientation to the probe in a tensile testing configuration.

7. The testing assembly of claim 1, wherein the stage plane is configured to reach temperatures of more than 400 degrees Celsius.

8. A heating system for use in testing at a scale of microns or less, the heating system comprising:
   a stage heater including:
      a stage plane having a central planar portion and a perimeter planar portion,
      a stage heating element distributed across the central and perimeter planar portions, wherein the stage heating element underlies the stage plane and continuously extends across the stage plane throughout the central and perimeter planar portions,
      two or more support mounts on opposed sides of the stage plane, and
      a first bridge extending from the stage plane to a first mount of the two or more support mounts, and a second bridge extending from the stage plane to a second mount of the two or more support mounts.

9. The heating system of claim 8, wherein the stage heater includes a heater body panel, and the stage plane, stage heating element, the two or more support mounts and the first and second bridges are included in the heater body panel.

10. The heating system of claim 8, wherein the stage heating element is distributed across the stage plane in a serpentine pattern extending from a first stage plane edge to a second stage plane edge and from a first stage plane end to a second stage plane end.

11. The heating system of claim 8, wherein the stage heater includes a temperature sensing element coextensive with the stage heating element.

12. The heating system of claim 8, wherein the two or more support mounts are laterally spaced from the stage plane by the first and second bridges, the first and second bridges having a cross sectional area in a section orthogonal to a direction of heat transfer toward the two or more support mounts smaller than a cross sectional area of the stage plane or either of the two or more support mounts in the direction of heat transfer.

13. The heating system of claim 8 comprising a stage adaptor, the stage adaptor including:
   an adaptor body,
   a stage assembly coupling feature coupled with the adaptor body, the stage assembly coupling feature configured to couple the stage adaptor with a stage assembly, and
   a stage heater coupling feature coupled with the adaptor body, the stage heater coupling feature configured to couple the stage heater with the stage adaptor.

14. A method of testing a sample with a testing assembly at a scale of microns or less comprising:
   heating a sample on a stage heater, heating the sample including heating a stage plane with a stage heating element distributed across the stage plane, the stage plane and the stage heating element extending from a central planar portion of the stage plane to a perimeter planar portion of the stage plane, the stage plane coupled with the sample;
   heating a probe with a probe heater, the probe heater coupled with the probe; and
   testing the sample by engaging the heated probe with the heated sample.

15. The method of claim 14, wherein heating the sample includes distributing heat over the entire stage plane according to the stage heating element distributed across the stage plane.

16. The method of claim 14, wherein heating the sample includes heating the stage plane to a temperature greater than 1100 degrees Celsius while two or more support mounts are passively heated to a temperature of 150 degrees Celsius or less.

17. The method of claim 14 comprising throttling heat transfer from the stage plane to two or more support mounts arranged on opposed sides of the stage plane, the two or more support mounts laterally spaced from the stage plane.

18. The method of claim 14 comprising controlling heating of the sample and the probe to substantially the same temperature before testing.

19. The method of claim 14, wherein testing includes one or more of indentation testing, compression testing, tensile testing or scratch testing of the sample with the heated probe.

20. The method of claim 14 comprising orienting the sample relative to the probe with a stage coupled with the stage heater and the sample, and wherein orienting the sample relative to the probe includes moving the sample in one or more degrees of freedom including rotating or tilting of the sample.

21. The method of claim 14, wherein testing includes electrically testing the sample with two or more electrical contacts in electrical communication with the sample.

* * * * *